US010420785B2

(12) United States Patent
Jacob et al.

(10) Patent No.: US 10,420,785 B2
(45) Date of Patent: *Sep. 24, 2019

(54) RAPIDLY DISPERSIBLE DOSAGE FORM OF TOPIRAMATE

(71) Applicant: APRECIA PHARMACEUTICALS LLC, Blue Ash, OH (US)

(72) Inventors: Jules Jacob, Yardley, PA (US); Lauren Beach, E. Newark, NJ (US); Thomas G. West, Lawrenceville, NJ (US); Donald C. Monkhouse, Radnor, PA (US); Henry L. Surprenant, Phoenixville, PA (US)

(73) Assignee: APRECIA PHARMACEUTICALS LLC, Mason, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/244,563

(22) Filed: Aug. 23, 2016

(65) Prior Publication Data

US 2016/0361335 A1    Dec. 15, 2016

Related U.S. Application Data

(63) Continuation of application No. 14/837,354, filed on Aug. 27, 2015, now Pat. No. 9,492,380, which is a continuation of application No. PCT/US2014/029168, filed on Mar. 14, 2014.

(60) Provisional application No. 61/791,592, filed on Mar. 15, 2013.

(51) Int. Cl.
| | |
|---|---|
| *A61K 9/00* | (2006.01) |
| *A61K 9/20* | (2006.01) |
| *A61K 9/50* | (2006.01) |
| *A61K 31/00* | (2006.01) |
| *A61K 31/7048* | (2006.01) |
| *A61K 9/70* | (2006.01) |
| *A61J 3/06* | (2006.01) |
| *A61K 31/357* | (2006.01) |

(52) U.S. Cl.
CPC ......... *A61K 31/7048* (2013.01); *A61J 3/06* (2013.01); *A61K 9/0056* (2013.01); *A61K 9/2009* (2013.01); *A61K 9/2018* (2013.01); *A61K 9/2027* (2013.01); *A61K 9/2054* (2013.01); *A61K 9/2072* (2013.01); *A61K 9/2095* (2013.01); *A61K 9/5015* (2013.01); *A61K 9/5031* (2013.01); *A61K 9/7007* (2013.01); *A61K 31/357* (2013.01)

(58) Field of Classification Search
CPC ..... A61J 3/06; A61K 31/357; A61K 31/7048; A61K 9/0056; A61K 9/2009; A61K 9/2018; A61K 9/2027; A61K 9/2054; A61K 9/2072; A61K 9/2095; A61K 9/5015; A61K 9/5031; A61K 9/7007

See application file for complete search history.

(56) References Cited

U.S. PATENT DOCUMENTS

| | | |
|---|---|---|
| 4,371,516 A | 2/1983 | Gregory |
| 4,642,903 A | 2/1987 | Davies |
| 4,855,326 A | 8/1989 | Fuisz |
| 5,178,878 A | 1/1993 | Wehling |
| 5,283,065 A | 2/1994 | Doyon |
| 5,380,473 A | 1/1995 | Bogue |
| 5,518,730 A | 5/1996 | Fuisz |
| 5,578,322 A | 11/1996 | Shiozawa |
| 5,607,697 A | 3/1997 | Alkire |
| 5,631,023 A | 5/1997 | Kearney |
| 5,738,875 A | 4/1998 | Yarwood |
| 6,106,861 A | 8/2000 | Chauveau |
| 6,136,347 A | 10/2000 | Pollinger |
| 6,471,992 B1 | 10/2002 | Yoo |
| 6,482,823 B1 | 11/2002 | Yu |
| 6,586,012 B2 | 7/2003 | Yu |
| 6,767,557 B2 | 7/2004 | Ulrich |
| 7,749,533 B2 | 7/2010 | Fu |
| 7,897,173 B2 | 3/2011 | Ziegler |
| 7,906,141 B2 | 3/2011 | Ziegler |
| 8,968,769 B2* | 3/2015 | Bunick ............... A61K 9/0056 264/5 |
| 2003/0133975 A1 | 7/2003 | Yoo |
| 2003/0143268 A1* | 7/2003 | Pryce Lewis ........... A61J 3/10 424/464 |
| 2005/0152976 A1 | 7/2005 | Chenevier et al. |
| 2006/0039981 A1 | 2/2006 | Murpani |
| 2006/0099245 A1* | 5/2006 | Kumar ............... A61K 9/0065 424/451 |
| 2006/0127479 A1 | 6/2006 | Kumaraperumal |
| 2006/0159758 A1 | 7/2006 | Gandhi |
| 2006/0182796 A1 | 8/2006 | Wu et al. |

(Continued)

FOREIGN PATENT DOCUMENTS

| | | |
|---|---|---|
| EP | 138441 A2 | 4/1985 |
| JP | 2003533470 | 11/2003 |

(Continued)

OTHER PUBLICATIONS

Ratnaparkhi et al. Formulation and In-Vitro Characterization of Nimorazole Mouth Dissolving Tablets. RJPBCS, Jul.-Sep. 2012, 3(3):303-308.*

(Continued)

*Primary Examiner* — Robert A Wax
*Assistant Examiner* — Olga V. Tcherkasskaya
(74) *Attorney, Agent, or Firm* — Daniel F. Nesbitt; Hasse & Nesbitt LLC

(57) ABSTRACT

A taste-masked rapidly dispersible dosage form of topiramate is provided. Wax coated particles of topiramate are included within a porous bound matrix. The topiramate retains its taste-masked form after dispersion in the mouth of a subject even though the particles are not coated with a polymeric material. The dosage form disperses in saliva or water in less than 2 min even though it has a high content of wax. It can be used to treat diseases or disorders that are therapeutically responsive to topiramate or a derivative thereof.

16 Claims, 1 Drawing Sheet

(56) References Cited

U.S. PATENT DOCUMENTS

| | | | |
|---|---|---|---|
| 2007/0092553 A1 | 4/2007 | Tengler et al. | |
| 2007/0154550 A1 | 7/2007 | Arti | |
| 2007/0218129 A1 | 9/2007 | Besse | |
| 2007/0224281 A1* | 9/2007 | Park | A61K 9/2077 424/495 |
| 2008/0085306 A1* | 4/2008 | Nangia | A61K 9/1635 424/458 |
| 2010/0278901 A1 | 11/2010 | Tengler et al. | |
| 2010/0285130 A1 | 11/2010 | Sanghvi | |
| 2011/0212171 A1 | 9/2011 | Venkatesh et al. | |
| 2012/0040001 A1 | 2/2012 | Koizumi | |
| 2012/0076858 A1 | 3/2012 | Kolter | |
| 2012/0207836 A1* | 8/2012 | General | A61K 9/006 424/485 |
| 2012/0207929 A1 | 8/2012 | Yoo | |

FOREIGN PATENT DOCUMENTS

| | | |
|---|---|---|
| JP | 2005509001 | 4/2005 |
| JP | 2010511633 | 4/2010 |
| JP | 2012056948 | 3/2012 |
| JP | 2012254974 | 12/2012 |
| WO | 9944581 A2 | 9/1999 |
| WO | 2005065647 | 7/2005 |
| WO | 2009106824 | 3/2009 |

OTHER PUBLICATIONS

Gandhi. Mouth Dissolving Tablets: A New Venture in Modern Formulation Technology. The pharma journal. 2012, 1(8):14-31.*
Yu et al. ("A novel fast disintegrating tablet fabricated three-dimensional printing" in Drug Development and Indust. Pharm. (2009), 35(12), 1530-1536).
"Hydroxypropyl cellulose", in USP29-NF24, Stage 6, Harmonization, (Dec. 2014), 3347.
"Hypromellose" in USP29-NF24, Stage 6, Harmonization, (Dec. 2014), 2375.
"Poloxamer" in USP29-NF24, (2006), 29(6), 3392.
"Povidone" in USP29-NF24, Stage 6, Harmonization, (Dec. 2011), 1777-1780.
"<811> Powder Fineness", in USP29-NF24, Stage 6, Harmonization, May 2012), 2754.
"<786> Particle Size Distribution Estimation by Analytical Sieving", in USP29-NF24, Stage 6, Harmonization, May 2012), 2720.
Signet Chemical Company, "Kolliphor P (LUTROL F)", available on Wayback Machine website at https://web.archive.org/web/20160625123654/http://www.signetchem.com:80/Signet-The-Complete-Excipients-Company-Product-Kolliphor-P-Lutrol-F, Jun. 25, 2015 (2 pages).

* cited by examiner

RAPIDLY DISPERSIBLE DOSAGE FORM OF TOPIRAMATE

CROSS-REFERENCE TO EARLIER FILED APPLICATIONS

The present application claims the benefit of and is a continuation of application Ser. No. 14/837,354 filed Aug. 27, 2015, which claims the benefit of and is a continuation of PCT/US2014/029168 filed Mar. 14, 2014, which claims the benefit of provisional application 61/791,592 filed Mar. 15, 2013, the entire disclosures of which are hereby incorporated by reference.

FIELD OF THE INVENTION

The present invention concerns a taste-masked rapidly dispersing (orodispersible) solid oral dosage form of topiramate. In particular, the dosage form disperses within a period of less than about fifteen seconds when placed in the mouth of a subject and the topiramate maintains its taste masking. The invention also relates to methods of use of the dosage form for the treatment of diseases, disorders or conditions that are therapeutically responsive to topiramate. A process for preparing the dosage form is also provided.

BACKGROUND OF THE INVENTION

Solid oral dosage forms containing Topiramate (TOP; 2,3:4,5-bis-O-(1-methylethylidene)-beta-D-fructopyranose sulfamate; disclosed in EP 138441) are known (FDA Electronic Orange Book). Topiramate is an anticonvulsant indicated for treating partial onset or primary generalized tonic-clonic seizures in epilepsy, for adjunctive therapy in Lennox-Gaustat syndrome, and migraine. It has also been used to treat bipolar disorder, borderline personality disorder, adjuvant for anti-psychotics, post-traumatic stress disorder, antipsychotic-induced weight gain, and other conditions as is recognized in the relevant art.

Topiramate is susceptible to heat and moisture. Degradation of topiramate is readily detected by changes in physical appearance i.e. discoloration to brown or black, and formation of sulfate ions, which can be measured by standard techniques. A typical solution to overcome this problem is to protect the drug by applying a coating which diminishes the contact of the outside environment with the active ingredient and to use volatile organic solvents while applying the coating.

TOP is dosed at high levels such as 400 mg per day (two 200 mg doses) for the treatment of epilepsy. That upper dose is achieved by dose escalation over a period of 6 weeks. However, young and elderly patients typically experience difficulty in swallowing solid oral dosage forms containing such high doses, especially because of the large amount of excipients included in known dosage forms. Difficulty in swallowing leads to poor patient compliance. Attempts to resolve this problem have lead to the development of oral liquid and injectable formulations. Stability, contamination and inaccurate dosing problems, however, are still associated with such dosage forms, and only tablets or capsules (including a sprinkle capsule) have been approved in the U.S. to date.

Given the high doses of TOP required per tablet, it is difficult to formulate rapidly dispersible solid oral dosage forms with sufficient hardness and friability suitable for storage and handling. Attempts to resolve such problems have been disclosed.

Orodispersible dosage forms disperse or disintegrate in the mouth in a minimal amount of saliva or water. Such dosage forms provide ease of swallowing, accuracy of dosing, and rapid therapeutic action. U.S. Pat. No. 7,749,533 to Fu et al. discloses a dosage form containing granules containing a drug, porous plastic substance, water penetration enhancer, binder and drug. The granules must be compressed in order to create the dosage form. U.S. Pat. No. 4,371,516 to Gregory et al. and U.S. Pat. No. 5,738,875 disclose freeze-dried dosage forms. U.S. Pat. No. 5,178,878 to Wehling et al. discloses a soft-compressed orodispersible dosage form. Effervescent dosage forms and quick release coatings of insoluble microparticles are described in U.S. Pat. Nos. 5,578,322 and 5,607,697. Freeze dried foams and liquids are described in U.S. Pat. Nos. 4,642,903 and 5,631,023. Melt-spun dosage forms are described in U.S. Pat. Nos. 4,855,326, 5,380,473 and 5,518,730. U.S. 20070218129 discloses an immediate release dispersible and orodispersible solid pharmaceutical composition having the form of particles with a size lower than 710 μm upon dispersion into water, wherein the formulation is made by wet granulation; however, the disintegration times range from 53 to 60 sec. U.S. Pat. No. 6,471,992, U.S. 2012-0207929 and U.S. 2003-0133975 disclose three-dimensionally printed rapidly dispersing dosage forms.

Topiramate is known to have an extremely bitter taste, which is disadvantageous in orodispersible dosage forms. A major requirement of any such solid form is that it must be palatable to reduce the risk of a patient neglecting to take the medication. In cases where the active ingredient is particularly unpalatable and somewhat unstable, it is difficult to prepare such solid forms, and in addition show good stability and bioavailability.

Taste-masked dosage forms for poorly tasting drugs have been developed. U.S. Pat. No. 6,767,557 to Ulrich suggests a reconstitutable powder containing drug encapsulated in a water insoluble enteric coating. U.S. Pat. Nos. 6,586,012 and 6,482,823 to Yu disclose a liquid formulation containing topiramate encapsulated in an acid soluble coating. U.S. 20120207836 to General suggests a film wafer formulation containing drug particles encapsulated in a cationic polyacrylate coating. U.S. 20120076858 to Kolter suggests a rapidly dispersible formulation containing drug particles encapsulated in a cationic polyacrylate coating. U.S. 20120040001 to Koizumi suggests a rapidly dispersible compressed dosage form comprising drug, starch, binder and molding agent. U.S. 20110212171 to Venkatesh discloses an orodispersible dosage form comprising topiramate particles coated with a water insoluble polymer. U.S. 20100285130 to Sanghvi suggests a film formulation comprising a complex of drug and ion exchange resin coated with an ingestible polymer. U.S. 20100278901 and U.S. 20070092553 to Tengler suggests a rapidly dispersible compressed dosage form comprising drug complexed to a resin. U.S. 20070154550 to Arti discloses an acrylate or ethyl cellulose coated powdered form of topiramate. U.S. 20060182796 to Wu discloses an acrylate and enteric polymer coated powder form of topiramate. U.S. 20060159758 to Gandhi a taste-masked formulation containing an acrylate polymer in combination with another polymer. U.S. Pat. No. 6,106,861 discloses a rapidly disintegrable multiparticulate tablet which disintegrates in the mouth in less than 40 seconds and includes excipients selected from disintegrating agents, binding agents, and an active ingredient. The active ingredient is in the form of microcrystals coated with a taste masking coating that includes polymethacrylates and cellulose polymers such as hydroxypropyl-methyl cellulose, hydroxypropyl cellulose and cellulose acetophthalates. U.S. Pat. No. 6,136,347 describes flavor-masked pharmaceutical compositions that include microcapsules coated with water insoluble neutral methacrylic acid ester copolymers and triethylcitrate. PCT application WO 99/44581 discloses a process for taste masking of topiramate by coating the core with a taste masking coating mixture. The taste masking mixture includes cellulose acetate, cellulose acetate butyrate, methylcellulose, ethylcellulose or an Eudragit, and a disintegrant. U.S. 20060127479 to Kumaraperumal discloses a taste-masked drug coated with an acrylate polymer. U.S. 20060039981 to Murpani discloses a taste-masked drug coated with an acrylate polymer.

Acceptable taste-masking in orodispersible dosage forms is difficult to achieve, especially with a drug such as TOP, since it is more difficult to mask the taste of a high-dose drug in such a dosage form. It is not possible to predict a priori which taste-masked form of TOP will be suitable for use in an orodispersible dosage form, since the process and components used to prepare the orodispersible dosage form would very likely alter the taste-masked TOP thereby forming unmasked TOP during preparation of the dosage form. Moreover, it is not possible to predict a priori whether a particular taste-masked form of topiramate will retain its taste masking when incorporated into a three-dimensionally printed dosage form due to the use of various ingredients during printing and use of heat during drying.

None of the above discloses a taste-masked rapidly dissolving solid oral dosage form containing TOP as described herein. It would be beneficial to provide a taste-masked rapidly-dispersing orodispersible solid oral dosage form containing TOP that exhibits sufficiently low friability and sufficient hardness to withstand storage and handling while at the same time exhibiting an extremely rapid disintegration rate and acceptable taste; however, no such suitable dosage form containing TOP has been disclosed in the art. In particular, no such three-dimensionally printed dosage form has been disclosed.

SUMMARY OF THE INVENTION

The present invention seeks to overcome some or all of the disadvantages inherent in the art. The present invention provides an orodispersible solid dosage form, as described herein, comprising topiramate as the primary or sole active ingredient, wherein the dosage form comprises a bound matrix that disperses/disintegrates in 2 min or less in a volume of 15 ml or less of water or saliva and the topiramate remains taste-masked even after dispersion of the dosage in the mouth of a subject. The matrix disperses in the mouth of a subject to which it is administered, thereby facilitating swallowing and administration. In some embodiments, the disintegration time is determined according to USP <701>.

In some aspects, the invention provides a taste-masked rapidly dispersible, i.e. orodispersible, dosage form and administration thereof for the treatment of diseases, conditions or disorders that are therapeutically responsive to topiramate. The rapidly dispersible solid dosage form comprises a three-dimensionally printed matrix comprising TOP and bulk material. The matrix is formed by deposition of a printing fluid to a powder, whereby the particles of the powder become bound by binder. The matrix is porous with a defined overall bulk density, disintegration (dispersion) time in aqueous fluid, dissolution time in aqueous fluid, and moisture content. The matrix provides a balance of improved taste, sufficient hardness, low friability and suitable dispersion time in a small volume of aqueous liquid.

The topiramate is included in the matrix and bulk material as taste-masked particles comprising topiramate and at least one waxy material. In general, the weight percentage of topiramate does not exceed the total weight percentage of waxy material(s). The weight ratio of topiramate to total waxy material is typically about 50:50 to about 20:80, about 50:50 to about 30:70, or about 50:50 to about 40:60.

In some embodiments, prior to being coated with waxy material, topiramate (TOP) particles typically have an average or mean particle size in the range of about 30-50 microns (volume mean diameter, VIVID), and/or have a D90 of less than about 200 microns, a D90 of less than about 150 microns, a D90 (particle diameter corresponding to 90% of the cumulative undersize distribution) of less than about 125 microns, a D90 of less than about 100 microns, a D90 less than 65 microns, a D90 of about 50 to about 70 microns, and/or have a D50 (median particle diameter; particle diameter corresponding to 50% of the cumulative undersize distribution) of less than about 100 microns, a D50 of less than about 75 microns, a D50 of less than about 60 microns, a D50 of less than about 50 microns, a D50 of less than about 40 microns, a D50 of about 30 to about 50 microns, and/or have a D10 (particle diameter corresponding to 10% of the cumulative undersize distribution) of less than about 50 microns, a D10 of less than about 40 microns, a D10 of less than about 30 microns, a D10 of less than about 20 microns, a D10 of about 5 to about 10 microns. After coating with waxy material, the coated particles typically have an average or mean particle size in the range of about 60 to about 250 microns, and/or have a D90 of less than 150 microns, a D90 of less than 125 micros, a D90 of less than 110 microns, and/or have a D50 of less than 120 microns, a D50 of less than 100 microns, a D50 of less than 75 microns, and/or have a D10 of less than 75 microns, a D10 of less than 50 microns, a D10 of less than 40 microns. TOP can be present as a mixture of two or more different native drug powders each having its own native particle size distribution and/or method of preparation.

The taste-masked particles have an average, mean or median particle size in the range of about 50 microns to about 400 microns, about 50 microns to about 300 microns, about 50 microns to about 250 microns, about 60 microns to about 250 microns, about 60 microns to about 100 microns, or about 75 microns to about 250 microns. The taste-masked particles may have a D10 of 5-20 microns, a D50 from 30-60 microns and/or a D90 of 90-120 microns. The taste-masked particles can be present as a mixture of two or more different powders each having its own effective particle size distribution and/or method of preparation.

In some embodiments, topiramate is present in crystalline form in the coated particles. All polymorphs of topiramate are contemplated. It can also be present in crystalline form prior to coating. The crystallinity of topiramate or any other material can be determined by differential scanning calorimetry (DSC) to determine the presence of amorphous material. In some embodiments, topiramate is present in amorphous form in the coated particles.

The invention also provides a taste-masked orodispersible dosage form comprising a three-dimensionally printed matrix comprising bound particles of wax-coated topiramate, sweetener, binder, and surfactant, wherein the particles are bound by binder. The particles forming the matrix are not bound by topiramate. The printing fluid does not substantially dissolve topiramate during a three-dimensional printing process. The matrix optionally further comprises disintegrant.

One aspect of the invention provides a taste-masked orodispersible three-dimensionally printed matrix comprising:

bound particles of taste-masked wax-coated topiramate, at least one sweetener, at least one binder, and optionally at least one disintegrant;
at least one surfactant, and at least one glidant; wherein
the particles are bound by binder;
the matrix is porous and non-compressed;
the matrix disperses in less than 90 sec in a volume of 15 ml of aqueous fluid; and
the weight ratio of topiramate to wax in the particles ranges from 20:80 to 50:50.

Some embodiments of the invention include those wherein: a) the wax coated particles of topiramate are prepared by spray congealing a mixture comprising molten wax and particles of topiramate; b) the wax is not an ionic polymer or copolymer, an acrylate polymer or copolymer, a methacrylate polymer or copolymer, or an enteric polymer or copolymer; c) the wax coating comprises one or more, one, two, or three different waxes; d) the surfactant is present in an amount ranging from 0-2% wt based upon the final weight of the dosage form; e) the total amount of wax coated particles ranges from 20-50% wt based upon the final weight of the dosage form; f) the hardness of the matrix ranges up to about 1.0 kiloponds; g) binder is introduced into the matrix by way of printing fluid used to form the matrix; h) binder is introduced into the matrix by way of bulk powder used to form the matrix; i) the matrix comprises about 25 mg to about 200 mg of topiramate; j) the matrix comprises 10 to 40 printed incremental layers; k) the thickness (height) of an incremental layer ranges from 0.008 inches to 0.012 inches; l) the at least one sweetener is present in an amount range from 0-2% wt or >0 to about 2% wt based upon the final weight of the dosage form; m) the at least one binder is present in an amount range from >0 to about 20% wt based upon the final weight of the dosage form; n) the optional disintegrant is present in an amount range from 0-30% wt based upon the final weight of the dosage form; o) the at least one glidant is present in an amount range from 0-2% wt based upon the final weight of the dosage form; and/or p) surfactant is present in the wax-coated topiramate particles.

A method of treating a disease or disorder that is therapeutically responsive to topiramate is provided. The method comprises daily administering one, two or three dosage forms of the invention to a subject in need thereof over a treatment period lasting days, weeks or months thereby reducing or eliminating one or more symptoms of the disease or disorder.

A method of preparing a taste-masked orodispersible dosage form is also provided. The method comprises forming a porous matrix as described herein by forming incremental layers of powders and depositing printing fluid on each incremental layer to bind disintegrant, binder, surfactant, glidant, sweetener and wax coated particles of topiramate into a non-compressed porous matrix.

The invention includes all combinations of the aspects, embodiments and sub-embodiments disclosed herein.

BRIEF DESCRIPTION OF THE FIGURES

The following figures form part of the present description and describe exemplary embodiments of the claimed invention. The skilled artisan will, in light of these figures and the description herein, be able to practice the invention without undue experimentation.

DETAILED DESCRIPTION OF THE INVENTION

Figure 1:
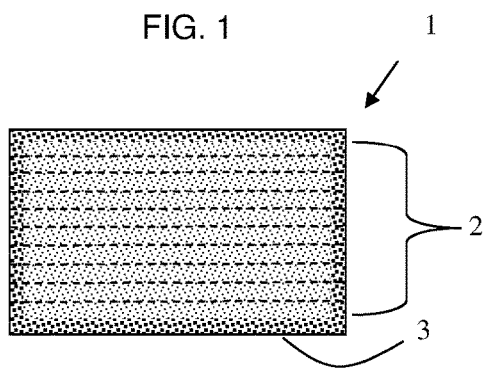
FIG. 1 depicts a sectional front elevation of an orodispersible dosage form made from a three-dimensionally printed matrix comprising sequentially-formed incremental layers of bound bulk material.

As used herein and unless otherwise specified, the term topiramate refers to the drug in underivatized or derivatized form. Topiramate also includes a topiramate derivative such as topiramate palmitate. Topiramate also includes novel salts of topiramate, and pharmaceutically acceptable polymorphs, solvates, hydrates, dehydrates, co-crystals, anhydrous, or amorphous forms thereof, as are described in U.S. Pat. No. 7,351,695, hereby incorporated by reference.

The present invention provides a taste-masked orodispersible dosage form comprising particles of topiramate coated with one or more waxy materials. The dosage form comprises a non-compressed matrix of particles bound by binder. The matrix comprises wax-coated particles of topiramate, glycerin, binder, surfactant and optional disintegrant. The matrix is porous and disperses within less than 90 sec when placed in a minimal amount of water. The dosage form provides improved taste-masking and rapid dispersion as compared to other three-dimensionally printed dosage forms comprising polymer-coated particles of topiramate, cyclodextrin complex of topiramate, and others. The wax-coated particles are preferably prepared by spray-congealing a melt comprising topiramate and at least one wax material.

Various different three-dimensionally printed (3DP) dosage forms comprising coated particles of topiramate were prepared according to Example 3. Comparator coated particles had been prepared by ion exchange complexation, hot melt extrusion, roller compaction, supercritical fluid coating, complexation with cyclodextrin, or fluid bed coating. The resulting 3DP dosage forms were evaluated by several subjects for taste to determine which if any of the comparator coated particles provided sufficient taste-masking of topiramate. It was determined that none of the comparator formulations provided adequate taste-masking. It is believed that the printing fluid might be dissolving a part of the surface coating of the comparator coated particles during the printing and/or drying step of the 3DP process.

On the other hand, the 3DP dosage forms of the invention which comprise spray-congealed wax coated particles of topiramate provided excellent taste-masking. Even after dispersion in the mouth, the bitter taste of topiramate was not apparent to the subjects. The inventors could not have predicted a priori which type of taste-masked coated particles would be suitable for preparation of a taste-masked orodispersible 3DP dosage form. Accordingly, the present inventors have discovered that one can achieve acceptable taste-masking in a topiramate-containing 3DP dosage form without having to coat the topiramate with a polymeric material.

The topiramate is coated with at least one waxy material, which is not an ionic polymer or copolymer, an acrylate polymer or copolymer, a methacrylate polymer or copolymer, or an enteric polymer. Inclusion of a waxy material in a 3DP matrix, however, presents substantial challenges in creating dosage forms that possess sufficient hardness. The wax tends to soften the matrix, especially when the matrix comprises a substantial weight percentage of coated particles. The wax also tends to increase the dispersion time of a 3DP orodispersible dosage form. As a result, the physical properties of the 3DP dosage form can be different that desired.

It has been determined that inclusion of a surfactant in the printing fluid aids in ensuring rapid dispersion of the 3DP dosage form without sacrificing taste-masking. Surfactant may also be included in the wax-coated topiramate particles. This result is unexpected as surfactants are typically used in cleaning compositions to dissolve waxes. Before evaluation of the surfactant employed herein, the inventors could not a priori predict whether or not the surfactant would interfere with taste-masking.

The weight ratio of topiramate to waxy material can be varied; however, doing so will have an impact upon hardness, dispersion time, taste-masking, size and drug dose of the dosage form. If the waxy material content is too low, the taste-masking will be insufficient. If the waxy material content is too high, the hardness will be too low, the dispersion time will be too high, and the size of the dosage form would have to be increased substantially in order to include a suitable dose of topiramate therein.

It has been determined that the waxy material should be present in at least equivalents amounts as topiramate and is preferably present in excess amounts over topiramate. In some embodiments, the weight ratio of topiramate to waxy material is in the range of 20:80 to 50:50, 30:70 to 50:50 or 40:60 to 50:50.

The waxy coating can comprise one or more, one, two, or three different waxes.

In some embodiments, the waxy material is selected from the group consisting of glyceryl dipalmitostearate, glyceryl distearate, glycerol palmitostearate, glyceryl dibehenate, mono and diglyceride mixture, glycerol monostearate, beeswax, carrnuba wax, or cetyl esters wax. The waxy material is preferably glyceryl dipalmitostearate or glyceryl distearate.

A surfactant aids in dispersion of the 3DP dosage form when placed in a minimal amount of water. The surfactant serves to enhance wetting of the waxy coated particles without reducing or eliminating taste-masking. The surfactant does not dissolve the coating to any substantial degree when the dosage form is administered to a subject. It need only be present in an amount sufficient to enhance dispersion as compared to another 3DP dosage form excluding the surfactant. If the surfactant is present in too high of an amount, however, it will negatively impact mouth feel, performance and/or physical properties of the dosage form. It may also negatively impact taste, due to the taste of the surfactant itself. In some embodiments, the surfactant is present in an amount ranging from 0.0-2.0%, 0.1%-1.0%, 0.2%-0.9% wt. based upon the weight of the finished dosage form.

The rapidly dispersible dosage form can disperse (disintegrate) in less than about 3 min, less than about 2.5 min, less than about 2 min, less than about 1.5 min, less than about 60 seconds, less than about 30 seconds, in about 15 seconds or less, in about 10 seconds or less, in about 5 sec or less, in about 4 sec or less, or in about 3.5 sec or less when placed in a small volume of aqueous fluid, such as a saliva, gastric fluid and/or a sip of water. In some embodiments, the dispersion (disintegration) time is measured in a small volume of 20 ml or less, 15 ml or less, 10 ml or less, 5 ml or less, 3 ml or less and at least 1 ml of an aqueous fluid. In some embodiments, the dispersion (disintegration) time is measured by swirling in a beaker with 15 ml of water. In some embodiments, the disintegration time is determined according to USP <701>.

The small volume of aqueous fluid can be a sip such as a volume 50 ml or less, 40 ml or less, 30 ml or less, 20 ml or less, 10 ml or less, 5 ml or less, 2.5 ml or less or 1 ml or less. The small volume can be at least 0.1 ml, at least 0.25 ml, at least 0.5 ml, at least 0.75 ml, at least 1 ml, at least 1.5 ml or at least 2 ml. All possible combinations of these volumes are contemplated. Suitable ranges for the small volume include 0.1 to 50 ml, 0.1 to 40 ml, 0.1 to 30 ml, 0.1 to 20 ml, 0.1 to 10 ml, 0.2 to 10 ml, 0.3 to 10 ml, 0.5 to 10 ml, 1 to 10 ml, 5 to 10 ml, 1 to 7.5 ml, 1 to 5 ml, 0.5 to 3 ml, or other such ranges. In a preferred embodiment, the sip may comprise about a tablespoon (15 ml) of water. Preferably a sip is about 2 to about 30 ml, about 10 to about 15 ml (1 tablespoon) or about 13 ml of water (fluid).

In some embodiments, the dosage form comprises not more than 10% wt., not more than 7.5% wt., not more than 5% wt., not more than 4% wt., not more than 3% wt., not more than 2.5% wt., not more than 2% wt. or not more than 1.5% wt. moisture as determined by loss on drying (LOD) at 120° C. In some embodiments, the dosage form comprises at least 0.1% wt., at least 0.2% wt., at least 0.5% wt., at least 0.75% wt., at least 1% wt., at least 1.5% wt., at least 2% wt., at least 2.5% wt., at least 3% wt., at least 4% wt., or at least 5% wt. moisture as determined by loss on drying at 120° C. In some embodiments, the dosage form comprises 0.1 to 10% wt, 0.2 to 7.5% wt, 0.5 to 5% wt, 0.5 to 4% wt or 1 to 3% wt moisture. All combinations of these various limits are within the scope of the invention.

In some embodiments, the overall hardness (as determined by a tablet breaking force assay according to USP <127>) of the matrix ranges from 0.5 kp to about 5 kp or from about 0.5 kp to about 2 kp. In some embodiments, the overall hardness is at least 0.5 kp, at least 1.0 kp or at least 1.5 kp. In some embodiments, the overall hardness is no more than 3.0 kp, no more than 2.0 kp or no more than 1.0 kp. In some embodiments, the dosage form is found to be adequate for handing and administration without providing a numerical result on a tablet hardness tester.

The term friability is the tendency of the matrix to lose material from its outer edges and surfaces upon mechanical insult. Friability is reduced by increasing the hardness. In some embodiments, the dosage form possesses a friability of less than about 25%, preferably less than about 10% as determined according to USP <1216> and as further described below.

In some embodiments, the porosity of the matrix ranges from about 10% to about 90% or from about 30% to about 70% of the dosage form volume.

In some embodiments, the bulk density of the dosage form (as determined by measurement and/or calculation) ranges from 150 (mg/mL) to about 1300 (mg/mL), or from about 400 (mg/mL) to about 1000 (mg/mL).

The rapidly dispersible dosage form of the invention is made by a three-dimensional printing (3DP) process. Suitable equipment assemblies for three-dimensional printing of articles are commercially available or are already in use: Massachusetts Institute of Technology Three-Dimensional Printing Laboratory (Cambridge, Mass.), Z Corporation's 3DP systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc. (Eden Prairie, Minn.), Objet Geometries (Billerica, Mass. or Rehovot, Israel), Xpress3D (Minneapolis, Minn.), and 3D Systems' system (Valencia, Calif.). Other suitable 3DP systems are disclosed in U.S. No. 20080281019, No. 20080277823, No. 20080275181, No. 20080269940, No. 20080269939, No. 20080259434, No. 20080241404, No. 20080231645, No. 20080229961, No. 20080211132, No. 20080192074, No. 20080180509, No. 20080138515, No. 20080124464, No. 20080121172, No. 20080121130, No. 20080118655, No. 20080110395, No. 20080105144, No. 20080068416, No. 20080062214, No. 20080042321, No. 20070289705, No. 20070259010, No. 20070252871, No. 20070195150, No. 20070188549, No. 20070187508, No. 20070182799, No. 20070182782, No. 20060268057, No. 20060268044, No. 20060230970, No. 20060141145, No. 20060127153, No. 20060111807, No. 20060110443, No. 20060099287, No. 20060077241, No. 20060035034, No. 20060030964, No. 20050247216, No. 20050204939, No. 20050179721, No. 20050104241, No. 20050069784, No. 20050061241, No. 20050059757, No. 20040265413, No. 20040262797, No. 20040252174, No. 20040243133, No. 20040225398, No. 20040183796, No. 20040145781, No. 20040145628, No. 20040143359, No. 20040141043, No. 20040141030, No. 20040141025, No. 20040141024, No. 20040118309, No. 20040112523, No. 20040012112, No. 20040005360, No. 20040005182, No. 20040004653, No. 20040004303, No. 20040003741, No. 20040003738, No. 20030198677, No. 20030143268, No. 20020125592, No. 20020114652, No. 20020079601, No. 20020064745, No. 20020033548, No. 20020015728, No. 20010028471, and No. 20010017085; U.S. Pat. Nos. 5,490,962, 5,204,055, 5,121,329, 5,127,037, 5,252,264, 5,340,656, 5,387,380, 5,490,882, 5,518,680, 5,717,599, 5,851,465, 5,869,170, 5,879,489, 5,934,343, 5,940,674, 6,007,318, 6,146,567, 6,165,406, 6,193,923, 6,200,508, 6,213,168, 6,336,480, 6,363,606, 6,375,874, 6,508,971, 6,530,958, 6,547,994, 6,596,224, 6,772,026, 6,850,334, 6,905,645, 6,945,638, 6,989,115, 7,220,380, 7,291,002 7,365,129, 7,435,368, 7,455,804, 7,828,022, 8,017,055; PCT International Publications No. WO 00/26026, No. WO 98/043762, No. WO 95/034468, No. WO 95/011007; and European Patent No. 1,631,440, which employs a cylindrical (radial or polar) coordinate-based system due to its construction. The entire disclosure of each of these non-foreign references is hereby incorporated herein.

The 3DP process described herein requires a powder layering system that forms a layer of powder and printing system that applies a printing fluid to the layer of powder according to a predetermined pattern, thereby forming an incremental printed layer. The printing fluid serves to form bound particles of powder, i.e. particles that are adhered to one another by one or more pharmaceutical excipients and/or one or more active ingredients. Incremental printed layers are formed one on top of another to vertically build the dosage form of the invention, thereby forming a dosage form comprising plural incremental printed layers. The process of spreading powder and depositing droplets is repeated until the desired number of layers for the dosage form is complete. The layers adhere to one another due to wicking of printing fluid from one layer to an adjacent other layer such that one or more excipients and/or one or more active ingredients adhere to both adjacent layers. Following completion of the initial three-dimensional structure, residual printing fluid is removed from or reduced in the dosage form by drying. The evaporation of solvent during the drying process leaves a matrix having a three-dimensional architecture comprising the particles of bulk material bound by solidified binder and/or other components including one or more active ingredients and/or any optional pharmaceutically acceptable excipients.

The three-dimensional printing process is normally conducted at ambient temperatures. The process can utilize a variety of printing fluids, including biologically compatible organic and aqueous solvents. The process is additive, whereby microscopic features are incorporated layer by layer, allowing a wide range of possible architectures to be constructed precisely on a sub-millimeter scale. Using three-dimensional printing to control simultaneously both the microscopic features and the macroscopic shape, the unique drug delivery systems of the present invention are obtained.

A particularly suitable printing assembly for three-dimensional printing of the instant dosage form includes build modules each having an incrementally height adjustable platform disposed within a cavity of the build modules, a powder layering system, a printing system, a printing fluid removal system and a dosage form handling system.

In general, at least two components are used in the three-dimensional printing process used to prepare the matrix of the rapidly dispersing dosage forms. The first component is the bulk powder material to be included in the incremental powder layers. The second component is the printing fluid (in some cases the fluid may also contain a binder) that is dispensed by a printhead onto the powder layer. In some embodiments, the bulk powder material is comprised of one or more pharmaceutically acceptable excipients and topiramate.

At least one component of the matrix must serve as a "binding agent" that binds particles of bulk powder together in the completed three-dimensional matrix. The binding agent produces adhesion between particles of the bulk powder. It is this adhesion that enables the dosage form to maintain a fixed shaped (geometry) under conditions of handling, storage, and administration. The strength and extent of the particle binding depends on the proportion of the binding agent either in the powder layer or deposited by the printing fluid, and is a function of the amount of fluid deposited. The term adhesion means the bonding or binding of particles of the bulk material to each other or to particles of another material present, such as particles of binder or active ingredient. There are various ways in which a binding agent can be included in the matrix. The invention contemplates a combination of one or two or more of these different ways.

In some embodiments of the method of preparation of the matrix, binding agent is present in the bulk powder, the printing fluid, or both. A binding agent in the printing fluid can be the same as or different than a binding agent in the bulk powder.

The binding agent can be a pharmaceutically acceptable binder. Including a "binder" as the binding agent in the printing fluid will result in a different internal microstructure of the dosage forms, particularly the pore size, than the internal microstructure of an otherwise same dosage form excluding binder in the binding solution. Upon printing, as the solvent evaporates, binder remains as a solid residue, which occupies void space in between powder particles, e.g. particles of disintegrant or drug. The resulting structure will have higher density compared to dosage forms fabricated without binder in the printing fluid.

The invention provides a process for the preparation of a rapidly dispersing solid dosage form comprising a three-dimensionally printed solid porous matrix comprising carrier, binder and drug, the process comprising: (a) providing a powdered mixture of one or more binders, one or more sweeteners, one or more humectants, one or more glidants, optionally one or more disintegrants, and drug, together with any optional pharmaceutically acceptable excipients; (b) forming an incremental layer of the powdered mixture; (c) applying to the incremental layer droplets of printing fluid according to a predetermined pattern to form a printed incremental layer; (d) repeating (b) and (c) a predetermined number of times, thereby providing a three-dimensionally printed moist matrix; and (e) removing printing fluid from the moist matrix, thereby providing three-dimensionally printed solid porous matrix having a composition, moisture content, porosity, overall bulk density, hardness, matrix dispersion time, in vitro drug dissolution time, in vitro dispersion behavior, in vivo pharmacokinetic behavior, structure, incremental layer thickness, drug particle size, disintegrant particle size, drug content, and/or friability within the ranges specified herein.

The dosage form of the present invention may be further shaped as desired to facilitate placement thereof in the buccal cavity of a subject. One such embodiment may be a wafer-like shape, donut, ring, tube, cube, spheroid, ellipsoid or rectangular box. In some embodiments, a donut shape may improve the dispersion time versus a shape of similar volume and composition but having no through-hole. In some instances of those embodiments, the dispersion or disintegration time may decrease by 50-80%.

FIG. 1 depicts a sectional front elevation of an orodispersible dosage form (1) made from a three-dimensionally printed matrix comprising sequentially-formed incremental layers of bound bulk material (2-3). The exterior surfaces (3) envelope a middle portion (2). The exterior surfaces have a greater hardness than the interior portion. This dosage form is made by three-dimensionally printed plural incremental layers. The bottom incremental layer, which defines the lower surface, and the upper incremental layer, which defines the upper surface, and the circumferential surfaces (left and right of the middle portion) are harder than the interior portion. The increased hardness is achieved by using a higher saturation level, higher content of binder or as otherwise described herein. The increased hardness at the periphery of the incremental layers of the middle portion is achieved by increasing the saturation level and/or content of binder at the periphery, but not the center (non-peripheral portion) of the respective incremental layers.

Figure 2:
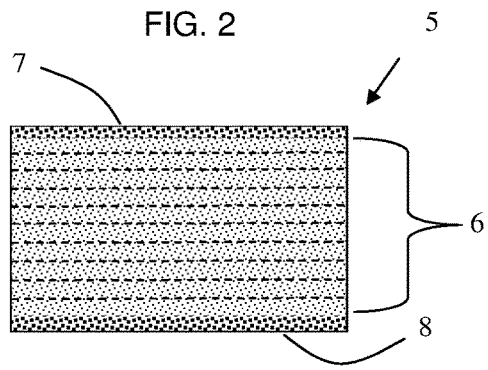
FIG. 2 depicts a sectional front elevation of an alternate embodiment of an orodispersible dosage form made from a three-dimensionally printed matrix.

FIG. 2 depicts a sectional front elevation of an alternate embodiment of an orodispersible dosage form (5) made from a three-dimensionally printed matrix. The bottom incremental layer, which defines the lower surface (8), and the upper incremental layer, which defines the upper surface (7) are harder than the interior portion (6) comprising plural incremental layers. The dosage forms (1) and (5) differ primarily in the process used to print the middle incremental layers, the layers of (6) not having a periphery with increased hardness.

Figure 3A:
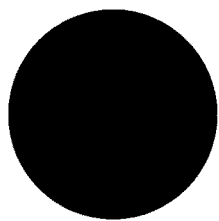
FIGS. 3A-3E depict various different printing patterns that can be used to apply printing fluid to incremental layers of powder.
Figure 3B:
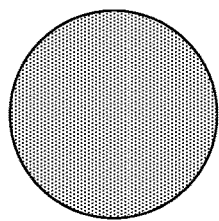
Figure 3C:
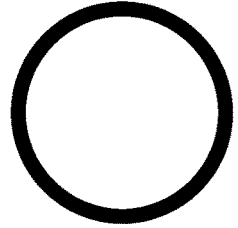
Figure 3D:
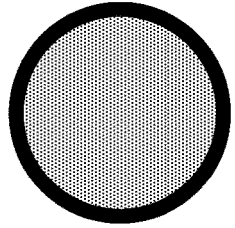
Figure 3E:
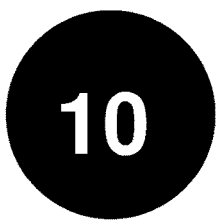

FIGS. 3A-3E depict the top plan view of three different print patterns that can be used to prepare the printed incremental layers of a 3DP orodispersible matrix of the invention. Even though each print pattern is depicted as being circular, substantially any geometry can be used, e.g. circle, oval, square, rectangle, oblong circle, etc. FIG. 3A depicts a first solid print pattern wherein substantially the same full, heavy or higher saturation level is used throughout the entire print area. FIG. 3B depicts a second solid print pattern wherein substantially the same medium, low, light or lower saturation level is used throughout the entire print area. This second solid pattern is referred to as a grayscale pattern since it has a reduced saturation level. FIG. 3C depicts an annular (hollow) print pattern wherein printing fluid is applied to the periphery of the print area but not toward the center of the print area. FIG. 3D depicts a combination annular and grayscale print pattern wherein printing fluid is applied to the periphery of the print area at a higher saturation level and toward the center of the print area at a grayscale (reduced) saturation level. FIG. 3E depicts an indicum print pattern wherein substantially the same saturation level is used throughout the entire print area except in the indicum region(s) wherein no printing fluid is applied thereby forming a recessed indicum in the surface of the final dosage form without pressing into the article as would be done with known techniques such as debossing or engraving.

In some embodiments, the dosage form comprises (consists essentially of or consists of) the following types of printed incremental layers: a) plural layers of first solid print pattern, and plural layers of combination annular and grayscale print pattern; b) plural layers of first solid print pattern, plural layers of annular print pattern, and plural layers of combination annular and grayscale print pattern; c) plural layers of first solid print pattern, plural layers of annular print pattern, plural layers of combination annular and grayscale print pattern, and plural layers of indicum print pattern; d) plural layers of first solid print pattern, plural layers of annular print pattern, plural layers of combination annular and grayscale print pattern, plural layers of first solid print pattern, and plural layers of indicum print pattern; e) plural layers of first solid print pattern, plural layers of grayscale print pattern, and plural layers of first solid print pattern; f) plural layers of grayscale print pattern; g) plural layers of combination annular and grayscale print pattern; h) plural layers of first solid print pattern; i) plural layers of first solid print pattern and plural layers of annular print pattern; j) plural layers of first solid print pattern, plural layers of combination annular and grayscale print pattern, and plural layers of indicum print pattern.

In some embodiments, the dosage form comprises (consists essentially of or consists of) the following types of incremental layers grouped into respective sections of the dosage form: a) a first end comprising plural layers of first solid print pattern; a middle portion comprising plural layers of annular print pattern and plural layers of combination annular and grayscale print pattern; and a second end comprising plural layers of indicum print pattern; b) a first end comprising plural layers of first solid print pattern; a middle portion comprising plural layers of combination annular and grayscale print pattern; and a second end comprising plural layers of first solid print pattern and/or plural layers of indicum print pattern; c) a first end comprising plural layers of first solid print pattern; a middle portion comprising plural layers of annular print pattern, plural layers of combination annular and grayscale print pattern; and a second end comprising plural layers of first solid print pattern and/or plural layers of indicum print pattern; d) a first end comprising plural layers of first solid print pattern; a middle portion comprising alternating groups of layers, wherein one group comprises plural layers of annular print pattern, and another group comprises plural layers of combination annular and grayscale print pattern; and a second end comprising plural layers of first solid print pattern and/or plural layers of indicum print pattern; e) plural layers of a first solid a first solid print pattern.

Figure 4A:
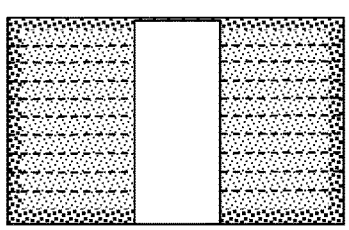
FIG. 4A depicts a sectional front elevation of an alternate embodiment of an orodispersible dosage form made from a three-dimensionally printed matrix.
Figure 4B:
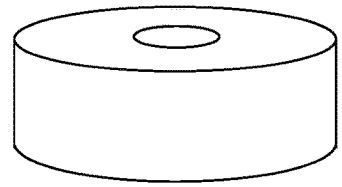
FIG. 4B depicts a perspective view of the dosage form of FIG. 4A.

The dosage form can also be shaped as a donut, ring or tube. FIG. 4A depicts an exemplary dosage form wherein the core of the dosage form about the vertical axis of the cylindrical shape has been left out or removed during manufacture of the dosage form. The diameter of the bore or hole can be in the range of 3-10 mm. In some embodiments, the hole is created via an unprinted zone within the dosage form and reaching at least one exterior surface such that unbound powder empties out. FIG. 4B depicts a perspective view of the dosage form of FIG. 4A.

The physical properties of the dosage form can be controlled by varying incremental powder layer thickness, powder composition, printing fluid composition, printing fluid saturation level (print density) on a layer, and identity and amount of the excipients included within the dosage form, e.g. identity and amount of disintegrant, binder, sweetener, surfactant. Some of these variables were studied to determine which of those are result effective variables with respect to dosage form hardness, bulk density, disintegration time, dissolution time, bioavailability, moisture content, taste, and friability. It was determined that the result effective variables include, at least, the amount of drug, amount of disintegrant, amount of binder, layer thickness, identity of some components, composition of the waxy material, and printing fluid saturation level.

Three-dimensional printing can have spatial descriptors in each of three different, typically orthogonal directions. In three-dimensional printing, fluid may be deposited in drops or in fluid units resembling drops. Drops may be deposited in a succession that forms a line corresponding to the motion of the printhead. The spacing between those drops is the drop-to-drop spacing. After completion of one line, another line may be deposited adjacent to the earlier-deposited line and separated from the earlier-deposited line by a distance that is a line-to-line spacing. After completion of printing on a layer of powder, another powder layer may be deposited, with each powder layer having a layer thickness. The powder layer thickness is the third descriptor.

In some instances, the spacing of droplets may be described in terms of the resolution of the printing system, often expressed as dots per inch (dpi), which is the reciprocal of droplet spacing. For example, resolutions of 300 and 600 dpi correspond to droplet spacing's of about 84.7 microns and about 42.3 microns, respectively. The drop-to-drop spacing (within a line), or the line spacing (spacing of droplets from one line to the next), or any other spacing of droplets may be described in terms of resolution expressed in dpi. In some instances, layer-by-layer instructions for making the dosage forms may consist of a series of pixelated images characterized by a resolution in dots-per-inch in each of two orthogonal linear directions. In some instances, these pixelated images are 1-bit monochrome images, alternately referred to as binary or bi-level images in which each pixel contains one bit of information (0 or 1) that may be represented as either black or white onscreen.

In some instances, the relative amount of binding in localized regions of the dosage form is achieved by "grayscaling" (i.e., use of a grayscale print pattern) in the dosage form design. In the case of 1-bit monochrome images used for machine instructions, grayscaling is achieved by changing the number of "black" pixels relative to "white" pixels in a chosen region of a dosage form, or in a chosen layer of a dosage form, or throughout a dosage form. Any other regions that may be "solid" by using all black pixels. In some embodiments, the dosage form design includes a "solid" exterior and a "grayscaled" interior. In some embodiments, grayscaling may be achieved with equally spaced black pixels amongst white pixels to reach an overall ratio of black to white pixels in the grayscaled region. In other embodiments, grayscaling may be achieved with randomly placed black pixels amongst white pixels to achieve an overall ratio of black to white pixels in the grayscaled region. In still other embodiments, grayscaling may be achieved with a chosen pattern (e.g., parallel lines, hashed pattern, dot pattern) of black pixels amongst white pixels to achieve an overall ratio of black to white pixels in the grayscaled region.

In three-dimensional printing, a voxel or unit volume may be defined by one drop-to-drop spacing in the fast axis direction of motion, by one line-to-line spacing in the slow axis direction of motion, and by one layer thickness in the vertical direction. Some of this unit volume is occupied by powder particles, and the remainder of the unit volume is empty space that collectively has a volume that is the void volume.

The saturation level (print density) describes how much of the void space in this unit volume is occupied by liquid which is dispensed in a drop or fluid unit which is dedicated to that particular voxel. The saturation level is the ratio of the dispensed fluid volume to the volume of empty space in the voxel. In general, in three-dimensional printing, saturation levels may be chosen to be slightly less than, or somewhere approximately equal to, 1.0 (void volume basis) also expressed as 100%. Excessively low saturation levels tend to result in poor structural integrity. Excessively high saturations levels tend to result in excessive bleeding of liquid beyond where the liquid was deposited. In the present dosage form, the saturation level during the step of applying printing fluid to a powder layer is varied as needed to provide the target hardness and dispersion time. The saturation level can to a powder layer range from about 85% to about 120%, about 10% to about 110%, about 15% to about 80%, about 20% to about 50% or about 15% to about 35% in aggregate across the dosage form, or otherwise in selected regions of the dosage form.

Suitable printing devices include those having a continuous jet printhead or those having a drop-on-demand printhead. A continuous jet printhead provides a continuous jet (uninterrupted series) of droplets while depositing printing fluid onto a powder layer. Continuous jet printheads may be used in conjunction with droplet deflection systems on order to select and control which droplets are deposited. A drop-on-demand printhead only deposits droplets of printing fluid onto the powder layer if it receives an instruction (demand, operational command) to do so. On some 3DP machines, a printhead scans (moves across and selectively applies fluid to) the surface of powder layer from left to right at a predetermined rate, e.g. a scan rate, to form a line of droplets. A high scan rate will result in a lower saturation level, and a low scan rate with result in a higher saturation level when comparing printing fluid deposition at a constant volume per unit time. When considering the situation where binder is present in the printing fluid, an increase in the print speed from 1.0 m/s to 2.0 m/s reduces the total volume of printing fluid deposited in the dosage forms by half. As the print speed increases, the bulk density (theoretical, calculated from the weight and dimensions of the dosage form) decreases. A simultaneous decrease in the dimensions and weight of the dosage forms is also seen. This decrease is attributed to three factors: (i) a decrease in the total volume of droplets deposited onto the powder results in a decrease in the extent of printing fluid spreading in the powder; (ii) a decrease in the mass of nonvolatile components from the printing fluid that remain behind; (iii) a greater tendency for loss of material from the edges of more friable dosage forms during separation from the unprinted powder. Increasing the print speed also decreases the flash time and the hardness and increases the friability of the dosage forms. This result is obtained because the proportion of binding agent from the printing fluid (or the level of activation of binding agent in the powder) decreases in the dosage forms as the print speed increases. An increase in the print speed also increases the void volume inside the dosage forms, as illustrated by an increase in the percent volume of the dosage forms penetrated by mercury at 30 psi (% intrusion).

When using a continuous jet printhead, the effective scanning rate is about 0.5 m/sec to 3.0 m/sec, and most preferably at about 1.75 m/sec. When using a drop-on-demand printhead, the printhead the effective scanning rate is about 0.1 m/sec to 1 m/sec, most preferably at about 0.15 m/sec to 0.5 m/sec.

The volume of individual droplets can be varied as desired. Increasing the volume of the droplet increases the saturation level and decreasing the volume of a droplet decreases the saturation level when comparing printing fluid deposition at a constant rate. When using a continuous jet printhead, the size of the fluid droplets delivered by the printhead preferably ranges from about 10 μm to about 150 μm in diameter. When using a drop-on-demand printhead, the size of the fluid droplets delivered by the printhead preferably ranges from about 20 μm to about 300 μm in diameter.

The flow rate of the fluid delivered by the printhead can be varied as desired. Increasing the flow rate increases the saturation level and decreasing the flow rate decreases the saturation level when comparing printing fluid deposition at a constant rate. As discussed herein, the printhead deposits droplets of printing fluid to form parallel lines thereof in the powder layer. When using a continuous jet printhead, the line spacing ranges from about 20 μm to about 1000 μm, about 50 μm to about 500 μm, or and preferably about 100 μm to 200 μm. When using a drop-on-demand jet printhead, the line spacing ranges from about 20 μm to about 300 μm, about 40 μm to about 100 μm, or preferably are about 55 μm to 75 μm.

The powder layering system and the height adjustable platform cooperate to form thin incremental layers of powder in the build modules. The total thickness (height) of the dosage form will be a function of the number and thickness of the incremental layers. The number of printed incremental layers typically ranges from 5 to 50, preferably 15 to 25 layers. A matrix will typically comprise (consist essentially of or consist of) 20 to 50, 20 to 40, 30 to 40 or 30 to 35 printed incremental layers. The "end" section of a dosage form will typically comprise 1 to 10, 1 to 7, 2 to 7, or 4 to 6 printed incremental layers. An end section with an indicum will typically comprise 2 to 10, 2 to 7, or 4 to 7 printed incremental layers. The balance of the printed incremental layers will comprise the middle portion, with respect to the vertical height, of the dosage form. The middle portion will typically comprise 5 to 40, 10 to 30, 10 to 20, or 20 to 30 printed incremental layers.

Dosage forms produced by the 3DP process described herein vary in size according to the content of TOP and of excipients required to provide dosage forms exhibiting the desired properties. If the matrix comprises a higher dose of TOP, then a larger wafer is required as compared to another 3DP dosage form having the same percentage but lower dose of TOP. If a higher percentage of TOP is used, the dosage form weight can be decreased correspondingly and vice versa.

The incremental layers are of a predetermined height (vertical thickness), which typically varies from 0.005 inches to 0.015 inches, 0.008 inches to 0.012 inches, 0.009 inches to 0.011 inches, 100-300 μm, 100-500 μm, about 200 μm, or about 250 μm. As thicker incremental layers are used, an increasing amount of printing fluid must be deposited on that layer to ensure adequate binding both within the plane of the layer and layer-to-layer. Conversely, for a thinner incremental layer a lesser amount of printing fluid must be deposited to obtain the same extent of binding. For a given amount of printing fluid deposited per layer, using a larger layer thickness will reduce (worsen) dosage form handleability and reduce (improve) dispersion time. If too thick of a layer is used for a given amount of fluid, laminar defects may form that cause the dosage form to easily fracture along the plane of the layers (delamination), or the dosage form itself may not have adequate strength to handle at all. In some embodiments, the thickness of the incremental layers ranges from 100-400 microns, 150-300 microns, or 200-250 microns. In one preferred embodiment, the layer thickness is 200 microns. In another preferred embodiment, the layer thickness is 250 microns.

One or more pharmaceutically acceptable excipients can be included in bulk powder material and/or the printing fluid. Each excipient may be independently selected upon each occurrence from a water soluble, aqueous fluid soluble, partially water soluble, partially aqueous fluid soluble, water insoluble or aqueous fluid insoluble excipient as needed to provide the required particle-to-particle binding in a printed matrix.

Most pharmaceutically acceptable excipients, both small molecules and polymers, can be employed, which allow a pharmaceutically active ingredient to be loosely encased in a porous structure (a matrix of bound particles) that is subject to rapid dispersion in the presence of an appropriate aqueous fluid, e.g., saliva. Some of these excipients, suitable for use in the three-dimensional printing process of the invention, are listed in the Handbook of Pharmaceutical Excipients (Eds. A. Wade and P. J. Weller, Second edition, American Pharmaceutical Association, The Pharmaceutical Press, London, 1994).

Suitable types of excipients include binder, disintegrant, dispersant, sweetener, glidant, flavorant, surfactant, humectant, preservative, and diluent. Although conventional pharmaceutical excipients may be used, they may not always function in precisely the same manner as with traditional pharmaceutical processing.

One or more binders can be included in the printed matrix. The binder may be included in either the powder material or in the printing fluid dispensed through the printhead. Adhesion of the particles to and/or by the binder occurs either when the binder is contacted by the printing fluid from the printhead or when it is present (i.e., soluble) in the printing fluid. The binder is preferably water soluble, aqueous fluid soluble, partially water soluble or partially aqueous fluid soluble. In some embodiments, the printing fluid comprises 0-20% wt, 5-15% wt or 8-12% wt of binder. In some embodiments, the bulk powder comprises >0% to 10% wt, 1% to 5% wt, 0-30% wt, 2-20% wt or 5-15% wt of binder. In some embodiments, the printed matrix comprises 0-30% wt, 2-20% wt or 5-15% wt of binder. In some embodiments, binder is absent from the printing fluid or absent from the bulk material. Suitable binders include water-soluble synthetic polymer, polyvinylpyrrolidone, hydropropylmethylcellulose (HPMC, hypromellose), copovidone (copolymer of vinyl acetate and vinyl acetate), partially or fully pregelatinized cornstarch, and hydroxypropylcellulose (HPC). A preferred binder is polyvinylpyrrolidone (PVP, povidone). In one preferred embodiment, the povidone (povidone K30) is characterized as exhibiting a k-value of approximately 27-32. In some embodiments, a water-soluble diluent aids binding of the matrix, with or without use of a traditional binder. Suitable diluents in this capacity include sugars and sugar-alcohols or polyols such as mannitol, sorbitol, xylitol, lactitol, erythritol. In this capacity, the diluent that aids binding may comprise 15-50%, or 30-45% of the printed matrix. In a preferred embodiment, the diluent that aids binding is mannitol.

One or more disintegrants can optionally be included in the printed matrix. The disintegrant can be present in the bulk powder. In some embodiments, the bulk powder comprises 0% to 30% wt, 2% to 25% wt, 5% to 15% wt, or 5% to 10% wt of disintegrant. Suitable disintegrants include microcrystalline cellulose (MCC), crospovidone (cross-linked polyvinylpyrrolidone), or a combination thereof. In one preferred embodiment, the disintegrant is microcrystalline cellulose. Suitable grades of AVICEL® microcrystalline cellulose are summarized in the table below. The dosage form can comprise one or a combination of the specified grades. All such embodiments containing single grades or a combination of grades are contemplated.

| Product Grades | Nominal Particle Size, μm | Moisture, % | LooseBulk Density, g/cc |
|---|---|---|---|
| Avicel DG | 45 | NMT 5.0 | 0.25-0.40 |
| Avicel PH-101 | 50 | 3.0 to 5.0 | 0.26-0.31 |
| Avicel PH-102 | 100 | 3.0 to 5.0 | 0.28-0.33 |
| Avicel HFE*-102 | 100 | NMT 5.0 | 0.28-0.33 |
| Avicel PH-102 SCG** | 150 | 3.0 to 5.0 | 0.28-0.34 |
| Avicel PH-105 | 20 | NMT 5.0 | 0.20-0.30 |
| Avicel PH-102 SCG | 150 | 3.0 to 5.0 | 0.28-0.34 |
| Avicel PH-200 | 180 | 2.0 to 5.0 | 0.29-0.36 |
| Avicel PH-301 | 50 | 3.0 to 5.0 | 0.34-0.45 |
| Avicel PH-302 | 100 | 3.0 to 5.0 | 0.35-0.46 |
| Avicel PH-103 | 50 | NMT 3 | 0.26-0.31 |
| Avicel PH-113 | 50 | NMT 2 | 0.27-0.34 |
| Avicel PH-112 | 100 | NMT 1.5 | 0.28-0.34 |
| Avicel PH-200 LM | 180 | NMT 1.5 | 0.30-0.38 |
| Avicel CE-15 | 75 | NMT 8 | N/A |

NMT means "not more than".

In another preferred embodiment, the disintegrant is crospovidone. When the disintegrant is crospovidone only, it may comprise 2-10% of the bulk powder. Crospovidone is a water-insoluble synthetic cross-linked homopolymer of N-vinyl-2-pyrrolidinone that is used as a superdisintegrant in conventional pharmaceutical processing, e.g., tableting. Several grades of crospovidone are available, including for example the product line offered by BASF that is distinguished by particle size for each grade: Kollidon® CL (110-130 microns), Kollidon® CL-F (20-40 microns), Kollidon® CL-SF (10-30 microns), and Kollidon® CL-M (3-10 microns).

The binder and disintegrant are key ingredients for controlling the hardness, friability and dispersion time of the matrix. The greater the amount of binder, the higher the hardness, the lower the friability and the slower the dispersion time. On the other hand, increasing the amount of disintegrant provides lower hardness, increased friability and a faster dispersion time. Accordingly, the matrix of the invention comprises a balanced amount of binder and disintegrant.

One or more sweeteners can be included in the printed matrix. The sweetener can be present in the bulk powder and/or in the printing fluid applied to the bulk powder. More efficient taste-masking is observed when at least one sweetener is present in at least the printing fluid. The printing fluid and the bulk powder can have at least one sweetener in common, e.g. the printing fluid and bulk powder each comprise the same sweetener and the bulk powder comprises an additional sweetener. In some embodiments, the printing fluid and the bulk powder each comprise sucralose or a glycyrrhizinic acid derivative. In some embodiments, the printing fluid and the bulk powder each comprise sucralose, and the bulk powder further comprises a glycyrrhizinic acid derivative. In some embodiments, the bulk powder comprises >0% to 5% wt, or >0% to 2% wt, or >0% to 1.5% wt of sweetener. In some embodiments, the printing fluid comprises >0% to 5% wt, >0% to 4% wt, >0% to 3% wt, >0% to 2% wt., 0.1% to 5% wt, 0.1% to 4% wt, 0.1% to 3% wt, 0.1% to 2% wt, 0.5% to 3% wt, or 1% to 3% wt sweetener.

Suitable sweeteners are selected from the group consisting of glycyrrhizinic acid derivative, e.g. magnasweet (monoammonium glycyrrhizinate), sucralose, other natural or artificial sweeteners, and a combination thereof. The preferred sweetener in the printing fluid is sucralose. Sweetener is present in at least the printing fluid but may also be present in the bulk powder.

Some ingredients that may be used for other purposes in the bulk powder may also contribute to sweetness. Examples of this are diluent powders such as mannitol, sorbitol, and xylitol.

One or more optional flavorants can be included in the matrix. The flavorant can be present in the bulk powder and/or the printing fluid. If present in the printing fluid, the flavorant is preferably water soluble, aqueous fluid soluble, partially water soluble or partially aqueous fluid soluble. If present in the bulk powder, the flavorant is preferably present in a form applied to a carrier powder before preparation of the bulk powder. Suitable carrier powders may include starches, modified starches, celluloses, and other powder capable of absorbing, adsorbing, encasing, or encapsulating the flavorant. In some embodiments, the printing fluid comprises 0-5% % wt, 0.01-1.0% wt or 0.05-0.5% wt of flavorant. In some embodiments, the bulk powder comprises 0.1% to 10% wt, or 1% to 10% wt, 2% to 8% wt, 3-7% wt of flavorant-incorporated carrier powder. In some embodiments, the printed matrix comprises 0-10% wt, 0.01-10% wt of flavorant. In some embodiments, the flavorant is absent from the printing fluid or absent from the bulk material. Suitable flavorants include peppermint, spearmint, mint, vanilla, orange, lemon, citrus, lime, grape, cherry, strawberry, chocolate, coffee or a combination thereof.

One or more surfactants can be included in the printing fluid and/or in the wax-coated topiramate particles. The surfactant is independently selected upon each occurrence. In some embodiments, the printing fluid comprises 0 to about 10%, >0% to about 7%, about 1% to about 5% wt of surfactant. In some embodiments, surfactant is present in the wax coated at a range of 0.3% to 15% wt, 1% to 12% wt, 1.5-9% wt, 2-6% wt. based upon the weight of wax coated particles included in the dosage form.

Suitable surfactants include polysorbate (PEG-ylated sorbitan (a derivative of sorbitol) esterified with fatty acid), poloxamer or a combination thereof. Suitable polysorbates include polysorbate 20 (Polyoxyethylene (20) sorbitan monolaurate), polysorbate 40 (Polyoxyethylene (20) sorbitan monopalmitate), polysorbate 60 (Polyoxyethylene (20)

sorbitan monostearate), polysorbate 80 (Polyoxyethylene (20) sorbitan monooleate), sodium lauryl sulfate, poloxamer (comprising a central (poly(propylene oxide)) flanked by two chains of (poly(ethylene oxide); e.g. LUTROL), low molecular weight polyethylene glycol (e.g. PEG 400).

Even though the dosage form can be preservative-free, one or more preservatives may optionally be included in the printing fluid or powder blend. Suitable preservatives include antifungal or antimicrobial preservatives such as methylparaben and propylparaben. In some embodiments, the printing fluid comprises 0.001% to 0.2% preservative.

One or more glidants can be included in the bulk powder. In some embodiments, the bulk powder comprises 0% to about 2% wt, >0% to about 1% wt of glidant. Suitable glidants include fumed silica (colloidal silicon dioxide).

In some embodiments, the pharmaceutically acceptable excipient in the bulk powder is selected from the group consisting of spray dried lactose, fructose, sucrose, dextrose, sorbitol, mannitol, and xylitol. These might be considered as diluents or low affinity binders. They can be included in the powder in amounts ranging from 0% to about 70%, about 10% to about 60, or about 20% to about 50% wt.

The matrix may also comprise glycerin (glycerol) introduced therein either by way of the bulk powder or the printing fluid. Glycerin can exhibit characteristics of a humectant, sweetener, preservative, lubricant, saponifier or solvent. The present inventors have discovered that glycerin unexpectedly behaves contrary to other excipients when included in a three-dimensionally printed dosage form. As noted above, increasing the amount of other excipients disclosed generally results in increased hardness with concomitantly increased disintegration time; however, increasing the amount of glycerin results in increased hardness but unexpectedly reduced disintegration time. The ability of glycerin to behave in this manner is particularly advantageous and has not been observed with any other material incorporated into a three-dimensionally printed orodispersible dosage form.

In some embodiments, glycerin is included in the printing fluid. Accordingly, the invention provides a printing fluid for use in three-dimensional printing wherein the printing fluid comprises glycerin, water, and at least one organic solvent. The invention also provides a three-dimensional printing method comprising: a) depositing a printing fluid comprising glycerin, water and at least one organic solvent onto at least one layer of powder; and b) reducing the content of water and solvent in the at least one layer, thereby forming a three-dimensionally printed porous matrix. The invention also provides a three-dimensional printing system comprising: a) a layer-forming system that forms layers of powder; and b) a printing fluid deposition system that deposits printing fluid onto the layers of powder, wherein the printing fluid comprises glycerin, water and at least one organic solvent.

In some embodiments, the printing fluid comprises 0% to about 20% wt, >0% to about 15%, >0% to about 10% or >0% to about 5% wt of glycerin. In some embodiments, the matrix comprises 0% to about 2% or >0% to about 1% wt of glycerin.

In some embodiments, the process of the invention employs a printing fluid comprising at least one or combination of pharmaceutically acceptable solvent for at least one material in the bulk powder and/or in the printing fluid itself. The printing fluid may comprise: a) a solvent for a material in the bulk powder; b) a solvent for a material in the printing fluid; or c) a combination thereof.

Embodiments of the process of the invention include those wherein the printing fluid comprises a solvent for: a) a binder in the bulk powder; b) a binder in the printing fluid; or c) a combination thereof.

The printing fluid can comprise about 75% to about 95%, or about 80% to about 90% % wt of water.

The printing fluid can comprise 0% to about 20%, >0% to about 20%, >0% to about 15%, >0% to about 10%, >0% to about 5% wt of at least one organic solvent. A suitable organic solvent is alcohol. Suitable alcohols include ethanol, methanol, propanol, isopropanol or a combination thereof. In some embodiments, the alcohol is ethanol.

It should be understood, that compounds used in the art of pharmaceutics generally serve a variety of functions or purposes. Thus, if a compound named herein is mentioned only once or is used to define more than one term herein, its purpose or function should not be construed as being limited solely to that named purpose(s) or function(s).

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps.

One or more of the components of the formulation can be present in its free base or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Suitable non-toxic salts include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Lists of other suitable salts are found in *Remington's Pharmaceutical Sciences*, 17$^{th}$. ed., Mack Publishing Company, Easton, Pa., 1985, p. 1418.

The invention also provides a method of administering topiramate to a subject in need thereof. The method comprises: (a) providing a rapidly dispersing, non-compressed matrix dosage form as described herein, and (b) inserting the dosage form into a moisture-containing body cavity, such as the mouth, of a subject in need thereof, the moisture being capable of dissolving the binder and dispersing the dosage form within a time period ranging from about one to about ninety seconds, thereby dispersing the dosage form in the body cavity. In some embodiments, the method further comprises the step of administering the dosage form to the subject with a sip (small volume) of fluid after the dosage form is placed in the mouth.

The invention also provides a method of treating a disease, disorder or condition that is therapeutically responsive to topiramate, the method comprising: a) administering to a subject in need thereof a three-dimensionally printed orodispersible matrix as described herein or as made by the process described herein. The matrix comprises topiramate, a bulk powder, and binder, and the matrix is dispersible in a small volume of fluid. The dosage and administration regimens detailed in the package insert for TOPAMAX® (commercial topiramate table described in NDA Application No. N020505) can be followed for administering the instant dosage form.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Example 1

Preparation of Coated Particles

The following process is used to make particles of topiramate coated with a waxy material. The following ingredients in the amounts indicated are used.

| INGREDIENT | AMT. (% WT.) | AMT. (% WT.) | AMT. (% WT.) | AMT. (% WT.) | AMT. (% WT.) | AMT. (% WT.) |
|---|---|---|---|---|---|---|
| Topiramate | 50 | 40 | 50 | 50 | 50 | 30 |
| GDPS | 50 | 60 | X | X | X | 70 |
| GELUCIRE | X | X | 50 | X | X | X |
| Vanillin | X | X | X | 50 | X | X |
| Poloxamer | X | X | X | X | 50 | X |

The coated particles are made by spray congealing a molten mixture of the topiramate and waxy material. A modified lab scale spray dryer SD45 (Buchi, model B-290) can be used.

The feed suspensions/solutions are prepared by melting the excipient and then adding the topiramate while stirring. A spray congealing unit is operated in open cycle mode, i.e., without recirculation of the congealing nitrogen. The gas flowrate is controlled by a Coriolis flow meter (Model R025S) and its temperature was adjusted using a refrigerator containing ethanol and dry ice. Both feeding vessel and nozzle are thermo-controlled using hot water. In addition all the feeding pipes are heated by means of an electric tracing to avoid the cooling of the suspension inside the pipes that could lead to clogging.

Before initiating each batch, the spray congealing unit is stabilized with nitrogen to obtain the desired inlet temperature. After stabilization of the inlet temperature, the solution/suspension is fed into the spray congealing equipment and atomized at the nozzle's tip. The small droplets are then congealed in the spray congealing chamber by the co-current congealing nitrogen. The stream containing the frozen particles of product leaves the chamber and enters the cyclone, where most of the solids are separated and collected in the collecting vessel.

If needed, feeding of viscous solutions/suspensions can be improved by coupling a hot melt extruder (run at approximately 100-150° C.) to the atomization system. The extruder forces a melt through the nozzle tip to cause atomization. A hot melt extrusion equipment assembly as described in U.S. Pat. No. 7,625,507, the entire disclosure of which is hereby incorporated by reference, can be used to prepare coated particles as described herein.

Approximately 50 g to 100 g of molten material are charged into the spray congealing unit. Typical operating conditions include:

Congealing nitrogen temperature (° C.): −45 to −25
Water temperature (° C.): 75-95
Atomizing nitrogen height in rotameter (mm): 25-60
Inlet temperature (° C.): −40 to −20
Outlet temperature (° C.): −10 to −3
Gas flowrate (kg/h): 15-30
Feed (melt) flowrate (ml/min): 1 to 10 or about 5
Holt melt extruder (HME) temp (if present) (° C.): 90-120
HME screw rotation (rpm): 50-100.

Following atomization, the droplets of molten material congeal in the chamber to form coated particles comprising topiramate and excipient.

Example 2

Determination of Crystallinity

A differential scanning calorimeter is used to determine the level of crystallinity of materials before and after inclusion in coated particles. The following process for the temperature ramping profile was used.

1. Equilibrate at −10° C.;
2. Ramp 10° C./min to 70° C.;
3. Isothermal for 5 min;
4. Ramp 10° C./min to −20° C.;
5. Equilibrate at −20° C.;
6. Modulate ±0.8° C. every 60 s;
7. Isothermal for 2 min;
8. Ramp 5° C./min to 250° C.;
9. Ramp 5° C./min to −10° C.

Example 3

Preparation of a Taste-Masked Three-Dimensionally Printed Orodispersible Dosage Form The following process is used to prepare a taste-masked three-dimensionally printed orodispersible dosage form comprising a matrix comprising bound coated particles of topiramate. The ingredients for the printing fluid and the bulk powder are used in the amounts indicated below:

| Printing fluid | I-A | I-B | I-C | I-D | I-E |
|---|---|---|---|---|---|
| Water (% wt) | 85 | 80 | 83 | 88 | 87 |
| Glycerin (% wt) | 5 | 5 | 5 | 0 | 5 |
| Ethanol (% wt) | 5 | 5 | 5 | 5 | 5 |
| Tween 20 (% wt) | 1 | 1 | 0 | 0 | 0 |
| Tween 80 (% wt) | 0 | 0 | 5 | 0 | 0 |
| Sucralose (% wt) | 2 | 2 | 2 | 2 | 2 |
| Sodium lauryl sulfate (SLS, % wt) | 2 | 2 | 0 | 0 | 0 |
| PEG 400 (% wt) | 0 | 5 | 0 | 0 | 0 |
| *Lutrol L44 (% wt) | 0 | 0 | 0 | 5 | 0 |
| Polysorbate (% wt) | 0 | 0 | 0 | 0 | 1 |

-continued

| Bulk powder: | II-A | II-B | II-C | II-D | II-E |
|---|---|---|---|---|---|
| Topiramate (coated particles) (% wt) | 40 | 40 | 40 | 40 | 40 |
| SLS (% wt) | 1 | 1 | 1 | 1 | 1 |
| Silica (colloidal silicon dioxide; % wt) | 1 | 1 | 1 | 1 | 1 |
| *PVP K29/32 (% wt) | 10 | 10 | 8 | 0 | 8 |
| Mannitol 50 C (% wt) | 24 | 24 | 30 | 30 | 30 |
| Avicel PH-101 (% wt) | 24 | 24 | 0 | 0 | 0 |
| *HPC LH-22 (% wt) (hydroxypropylcellulose) | 0 | 10 | 20 | 20 | 20 |
| *HPC-SL (% wt) | 0 | 0 | 0 | 8 | 0 |
| Kollidon CL-SF | 0 | 0 | 0 | 0 | 0 |

| | II-F | II-G | II-H | II-J | II-K |
|---|---|---|---|---|---|
| Topiramate (coated particles) (% wt) | 40 | 40 | 20 | 20 | 30 |
| SLS (% wt) | 1 | 1 | 1 | 1 | 1 |
| Silica (colloidal silicon dioxide; % wt) | 1 | 1 | 1 | 1 | 1 |
| PVP K29/32 (% wt) | 8 | 8 | 8 | 8 | 0 |
| Mannitol 50 C (% wt) | 30 | 30 | 50 | 50 | 68 |
| Avicel PH101 (% wt) | 0 | 0 | 0 | 0 | 0 |
| HPC LH-22 (% wt) (hydroxypropylcellulose) | 20 | 20 | 20 | 20 | 20 |
| HPC-SL (% wt) | 0 | 0 | 0 | 0 | 0 |
| Kollidon CL-SF | 0 | 0 | 0 | 0 | 0 |

| | II-L | II-M | II-N | II-O | II-P |
|---|---|---|---|---|---|
| Topiramate (coated particles) (% wt) | 30 | 30 | 40 | 40 | 40 |
| SLS (% wt) | 1 | 1 | 1 | 1 | 0 |
| Silica (colloidal silicon dioxide; % wt) | 1 | 1 | 1 | 1 | 1 |
| PVP K29/32 (% wt) | 4 | 4 | 10 | 10 | 0 |
| Mannitol 50 C (% wt) | 64 | 64 | 24 | 24 | 44 |
| Avicel PH101 (% wt) | 0 | 0 | 24 | 24 | 0 |
| HPC LH-22 (% wt) (hydroxypropylcellulose) | 0 | 0 | 10 | 10 | 0 |
| HPC-SL (% wt) | 0 | 0 | 0 | 0 | 15 |
| Kollidon CL-SF | 0 | 0 | 0 | 0 | 0 |

| | II-Q | II-R | II-S | II-T | IT-U |
|---|---|---|---|---|---|
| Topiramate (coated particles) (% wt) | 40 | 40 | 40 | 40 | 50 |
| SLS (% wt) | 0 | 0 | 0 | 0 | 0 |
| Silica (colloidal silicon dioxide; % wt) | 1 | 1 | 1 | 1 | 1 |
| PVP K29/32 (% wt) | 5 | 0 | 0 | 5 | 10 |
| Mannitol 50 C (% wt) | 49 | 51.5 | 46.5 | 49 | 29 |
| Avicel PH101 (% wt) | 0 | 0 | 0 | 0 | 0 |
| HPC LH-22 (% wt) (hydroxypropylcellulose) | 0 | 0 | 0 | 0 | 0 |
| HPC-SL (% wt) | 0 | 7.5 | 7.5 | 0 | 0 |
| Kollidon CL-SF | 5 | 0 | 5 | 5 | 10 |

*Lutrol L44 is poloxamer 124. HPC-SL is hydroxypropylcellulose having a molecular weight of approximately 100,000. HPC LH-22 is hydroxypropylcellulose having a molecular weight of approximately 135,000.

Any three dimensional printer equipment assembly, known or mentioned herein, can be used. An incremental layer of bulk powder of predetermined thickness is spread onto a prior layer of powder, and printing fluid is applied to the incremental layer as droplets according to a predetermined saturation level, line spacing and printing fluid flowrate to bind the particles therein. This two step process is completed until a matrix comprising the target amount of printed incremental layers.

The following printing parameters are used on a Z-Corp lab scale printer (Model Z310). The printer is equipped with a HP-10 printhead and is operated at a droplet size of 35 μn and line spacing of 450-600 μm. A solid print pattern is used throughout the dosage form. The specified combination of printing fluid formulation and bulk powder formulation is used.

| Printing Parameters: | III-A | III-B | III-C | III-D | III-E |
|---|---|---|---|---|---|
| Layer thickness (inches) | 0.01 | 0.01 | 0.01 | 0.01 | 0.01 |
| Saturation (%) | 110 | 110 | 110 | 110 | 110 |
| Printing fluid | I-A | I-A | I-A | I-A | I-B |
| Bulk Powder | II-A | II-B | II-C | II-D | II-E |

| | III-F | III-G | III-H | III-J | III-K |
|---|---|---|---|---|---|
| Layer thickness (inches) | 0.01 | 0.008 | 0.01 | 0.008 | 0.01 |
| Saturation (%) | 116 | 145 | 116 | 145 | 116 |
| Printing fluid | I-B | I-B | I-B | I-B | I-B |
| Bulk Powder | II-F | II-G | II-H | II-J | II-K |

| | III-L | III-M | III-N | III-O | III-P |
|---|---|---|---|---|---|
| Layer thickness (microns) | 0.01 | 0.008 | 0.01 | 0.01 | 0.01 |
| Saturation (%) | 116 | 145 | 116 | 116 | 116 |
| Printing fluid | I-B | I-B | I-C | I-D | I-D |
| Bulk Powder | II-L | II-M | II-N | II-O | II-P |

| | III-Q | III-R | III-S | III-T | III-U |
|---|---|---|---|---|---|
| Layer thickness (microns) | 0.01 | 0.01 | 0.01 | 0.008 | 0.01 |
| Saturation (%) | 116 | 116 | 116 | 116 | 116 |
| Printing fluid | I-D | I-D | I-D | I-D | I-D |
| Bulk Powder | II-Q | II-R | II-S | II-T | II-U |

The printed matrix is separated from loose unprinted powder and the printed matrix is dried by any suitable means to reduce the amount of solvent and moisture to a desired level, thereby producing the final taste-masked 3DP orodispersible dosage form. Dosage form weights ranged from 300 to 1200 mg or 330 to 1000 mg.

| Final composition | IV-A | IV-B |
|---|---|---|
| Topiramate (% wt) | 12-17 | 17-22 |
| SLS (% wt) | 2-3 | 2.5-3.5 |
| Colloidal silicon dioxide (% wt) | 0.5-1.5 | 0.5-1.5 |
| PVP (% wt) | 2-7 | 7-12 |
| Kollidon (% wt) | 2-7 | 7-12 |
| Mannitol (% wt) | 42-52 | 22-32 |
| MCC (% wt) | 0-15 | 0-10 |
| HPC (% wt) | 0-10 | 0-10 |

The dispersion time, hardness and acceptability of taste-masking of the dosage form are then determined.

Example 4

Preparation of a Taste-Masked Three-Dimensionally Printed Orodispersible Dosage Form The 3DP process described above is used to prepare a taste-masked three-dimensionally printed orodispersible dosage form comprising a matrix comprising bound coated particles of topiramate. The ingredients for the printing fluid and the bulk powder are used in the amounts indicated below:

| Printing fluid | V-A | V-B |
|---|---|---|
| Water (% wt) | 80-90 | 80-90 |
| Glycerin (% wt) | 0.05-20 | 1-8 |
| Alcohol (% wt) | 0.1-20 | 5-20 |
| First Surfactant (% wt) | 0.05-10 | 2-7 |

-continued

| | | |
|---|---|---|
| Sweetener (% wt) | 0.1-5 | 1-3 |
| Second Surfactant (% wt) | 0-10 | 0-5 |
| Bulk powder: | VI-A | VI-B |
| Topiramate (coated particles) (% wt) (35-45% TOP in particles) | 20-50 | 40-50 |
| surfactant (% wt) | 0-5 | 0-5 |
| Silica (colloidal silicon dioxide; % wt) | >0-5 | 0.5-2 |
| First Binder (% wt) | 20-50 | 30-50 |
| Second Binder (% wt) | | 5-10 |
| Disintegrant(s) (% wt) | 0-30 | 5-10 |

The printing fluid is applied to incremental layers of bulk powder by way of a 3DP process to prepare a taste-masked three-dimensionally printed orodispersible dosage form comprising a matrix comprising bound coated particles of topiramate.

| Final composition | VII-A | VII-B |
|---|---|---|
| Weight of dosage form (mg) | 335-365 | |
| Topiramate (% wt) | 15-20 | |
| Wax (% wt) | 20-30 | |
| Surfactant (% wt) | 2.5-3.5 | |
| Colloidal silicon dioxide (% wt) | 0.5-1.5 | |
| PVP (% wt) | 4.5-10 | |
| Mannitol (% wt) | 25-50 | |
| Crospovidone (% wt) | 4.5-10 | |
| Sweetener (% wt) | 1-2 | |

Example 5

Preparation of a Taste-Masked Three-Dimensionally Printed Orodispersible Dosage Forms with Varying Architecture Among Incremental Layers The 3DP process described above is followed; however, it can be conducted in several different ways to prepare dosage forms of different architecture varying in hardness and composition of incremental layers. The following processes provide a dosage form having greater hardness in the upper and lower surfaces as compared to the hardness of the interior portion of the dosage form. This tactic helps create sections within a dosage form with different mechanical properties. This approach is used to design dosage forms in which the composition of the top and bottom layers is different from the middle layers. This design allows the dosage forms to have stronger top and bottom layers, thereby increasing hardness and reducing friability, and a large middle portion with lower hardness, which enables the dosage form to disperse rapidly.

Method A:

In this process, the amount of binder deposited in different incremental layers or within different predefined regions within the same incremental layers is varied. The process of Example 3 is followed to prepare these dosage forms, except that the amount of binder, by way of the printing fluid, deposited onto the powder is varied among the incremental powder layers by using printing fluids differing in concentration of binder.

Method B:

The process of Example 3 is followed to prepare these dosage forms, except that the amount of printing fluid deposited onto the powder is varied among the incremental powder layers. The upper and lower incremental layers receive a higher amount of printing fluid and the incremental layers of the middle portion receive a lower amount of printing fluid.

Method C:

In this process, the printing pattern, employed for the upper and lower incremental layers of the dosage form, is a solid pattern (FIG. 3A). The printing pattern for the middle portion of incremental layers is a gray scale (FIG. 3 B).

Method D:

In this process, the printing pattern, employed for the upper and lower incremental layers of the dosage form, is a solid pattern (FIG. 3A). The printing pattern for the middle portion of incremental layers is an annular/hollow high saturation printing with no printing in the area surrounded by the annulus (FIG. 3C).

Method E:

In this process, the printing pattern, employed for the upper and lower incremental layers of the dosage form, is a solid pattern (FIG. 3A). The printing pattern for the middle portion of incremental layers is a combination of interior gray scale printing surrounded by an exterior high saturation printing (FIG. 3D).

Example 6

Preparation of a Non-Taste-Masked Three-Dimensionally Printed Orodispersible Dosage Form The process above is followed to prepare a non-taste-masked three-dimensionally printed orodispersible dosage form comprising a matrix comprising bound uncoated particles of topiramate. The only difference is that the topiramate particles are uncoated and therefore smaller in size than the particles of Example 3. Since the uncoated particles are approximately half the weight of coated particles, the weight of topiramate is adjusted accordingly to provide substantially the same dosage strengths.

Example 7

Characterization of Dosage Forms

The following procedures were used to characterize the three-dimensionally printed solid porous orodispersible matrices.

Friability

The matrices are analyzed for their resistance to breaking using the tablet friability test (USP protocol <1216>). The test employs a VanKel friabilator (model 45-2000, Varian, USA) equipped with a drum having the dimensions of 285 mm in diameter and 39 mm deep, which is rotated at 25 rpm for 100 revolutions. A minimum number of 10 dosage forms are tumbled at each revolution by a curved projection that extends from the middle of the drum to the outer wall. Thus, at each turn the tablets are caused to roll or slide and fall about 130 mm onto the drum or each other. All loose powder is removed from the tablets and they are weighted collectively before and after the 100 revolutions.

Hardness

The matrices are analyzed for overall hardness as determined by a tablet breaking force assay according to USP <127> ($31^{st}$ edition) using a VK 200 tablet hardness tester (Varian, US). The strength or hardness of the dosage forms is measured by a fracture test. A dosage form is centered between the jaws of the tester and force is applied until the dosage form fractures. The load at fracture is returned in kiloponds (kp). A kilopond is a metric unit of force measurement with 1 kp being equivalent to 9.807 Newtons. A minimum number of 6 dosage forms are tested.

Dispersion Time

The matrices are analyzed for dispersion time in aqueous fluid as follows using a Texture Analyzer (TA HP, Texture Technologies, US) equipped with a 5 Kg load cell and a 1.0 inch diameter acrylic probe (Stable Micro Systems). The dosage form is attached to the probe with double-sided adhesive tape. Under a constant 50 g force (Dor et al. in *Pharm. Dev. Technol.* (2000), 5(4), 575-577; and El-Arini et al. in *Pharm. Dev. Technol.* (2002), 7(3), 361-371), the dosage form is immersed in 3 ml of water at room temperature in a flat bottom aluminum weigh boat. The dispersion time test was conducted using the following parameters. A minimum of 5 dosage forms was tested.

| Test mode | Compression |
|---|---|
| Pre-test speed (mm/sec) | 5 |
| Test speed (mm/sec) | 8 |
| Post-test speed (mm/sec) | 10 |
| Target mode | Force |
| Force (g) | 50 |
| Hold time (sec) | 15 |
| Trigger type | Auto (force) |
| Trigger force (g) | 5 |
| Water volume (ml) | 3 |

The dispersion time observed for some of the dosage forms is approximately as follows.

| | III-H | III-J | III-K | III-L | III-M |
|---|---|---|---|---|---|
| Dispersion Time (s) | 52 | 59 | 34 | 58 | 90 |

| | III-N | III-O | III-Q | III-S | III-T | III-U |
|---|---|---|---|---|---|---|
| Dispersion Time (s) | 80 | 40 | 42 | 65 | 52 | 66 |

Bulk Density

The bulk density of the matrix is determined by measuring the weight of a dosage form and dividing that value by the calculated volume of the dosage form. The volume of a dosage form is calculated by measuring its dimensions and using the proper mathematical formula according to the shape of the dosage form. For example, for a cylindrical dosage form, the volume of which is calculated using the form $\pi*r^2*H$, wherein r is the radius of the water and H is its height. A dosage form weighing 0.5 g, having a height of 0.6 cm and a diameter of 1.1 cm, has a volume of about 0.57 cm$^3$, and a bulk density of about 0.877 g/cm$^3$, which is equivalent to about 877 mg/ml.

Dissolution of Topiramate

Dissolution testing is conducted according to the Guidance for Industry (Section 3.3.2; Waiver of In Vivo Bioavailability and Bioequivalence Studies for Immediate-Release Solid Oral Dosage Forms Based on a Biopharmaceutics Classification System. August 2000. Section Mc, p 7). The method of USP <711> was followed. Dissolution is performed using a USP Apparatus II (paddle) at 50 rpm using 900 mL of the following deaerated dissolution media: (1) 0.1N HCl; (2) 0.05 M sodium acetate, pH 4.5 buffer and (3) 0.05M KH$_2$PO$_4$, pH 6.8 buffer at 37° C.

Example 8

In Vivo Evaluation of Three-Dimensionally Printed Orodispersible Dosage Forms

This method is used to establish efficacy of the dosage form. Single dosage forms comprising topiramate are administered twice daily to a subject at 12-hour intervals. Administration is done by placing the dosage form in the mouth of the subject and optionally administering a sip (5-20 ml) of fluid to the subject. Within a short period of time, the dosage form disperses in the subject's mouth. Alternatively, the dosage form is dispersed in a minimal amount of fluid and then administered to the subject orally. The total daily dose of topiramate will typically be between 50-400 mg. The subject's pharmacokinetic profile is determined using known methods in the art. The subject level of therapeutic response to the dosage form is determined using known methods in the art.

If a dosage form is being evaluated for just its level of taste-masking, there is no need to determine a pharmacokinetic or therapeutic profile. The subject can merely comment on the taste of the dosage form as to whether or not it is acceptable.

As used herein, the term "about" or "approximately" are taken to mean±10%, ±5%, ±2.5% or ±1% of a specified valued. As used herein, the term "substantially" is taken to mean "to a large degree" or "at least a majority of" or "more than 50% of".

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A taste-masked rapidly dispersible dosage form comprising a three-dimensionally printed solid porous non-compressed bound matrix comprising:
   taste-masked wax-coated particles comprising drug particles and at least one wax, wherein the taste-masked wax-coated particles have a drug-to-wax weight ratio from 20:80 to 50:50, and wherein the wax is not an ionic polymer or copolymer, an acrylate polymer or copolymer, a methacrylate polymer or copolymer, or an enteric polymer or copolymer;
   at least one water soluble, aqueous fluid soluble, partially water soluble or partially aqueous fluid soluble binder selected from the group consisting of water soluble synthetic polymer, polyvinylpyrrolidone, hydroxypropylmethylcellulose, copovidone, pregelatinized cornstarch, hydroxypropylcellulose, lactose, fructose, sucrose, dextrose, sorbitol, mannitol, xylitol and a combination thereof; and
   at least one surfactant independently selected upon each occurrence from the group consisting of polysorbate, poloxamer, sodium lauryl sulfate, and a combination thereof; and wherein,
   the dosage form disperses in less than 90 sec when placed in aqueous fluid and the drug remains taste-masked.

2. The dosage form of claim 1 further comprising one or more components selected from the group consisting of at least one disintegrant, at least one sweetener, at least one diluent, glycerin and at least one glidant.

3. The dosage form of claim 2, wherein: a) the wax-coated particles are prepared by spray congealing a mixture of the drug particles and a molten form of the wax; b) the at least one wax comprises two or more different waxes; c) the at least one surfactant is present in an amount up to 2% of the final weight of the dosage form; d) the total amount of wax: coated particles is from 20% to 50% of the final weight of the dosage form; e) the hardness of the non-compressed bound matrix is up to about 1.0 kiloponds; f) the non-compressed bound matrix comprises from about 25 mg to about 200 mg of the drug; g) the non-compressed bound matrix comprises from 10 to 40 three-dimensionally printed incremental layers; h) the at least one sweetener is present in an amount up to about 2% of the final weight of the dosage form; i) the at least one water soluble, aqueous fluid soluble, partially water soluble or partially aqueous fluid soluble binder is present in an amount up to about 20% of the final weight of the dosage form; j) the at least one disintegrant is present in an amount up to 30% of the final weight of the dosage form; k) the at least one glidant is present in an amount up to 2% of the final weight of the dosage form; l) the wax-coated particles of drug further comprise a surfactant; or m) a combination thereof.

4. The dosage form of claim 3 wherein the wax: coated particles further comprise at least one surfactant present at 0.3% to 15% of the weight of wax-coated particles included in the dosage form.

5. The dosage form of claim 3, wherein the thickness of an incremental layer is from 0.008 inches to 0.012 inches.

6. The dosage form of claim 1, wherein: a) the wax-coated particles have an average or mean particle size of from about 60 microns to about 250 microns; b) the drug particles in the wax-coated particles have an average or mean particle size of from about 30 microns to about 50 microns; c) the dosage form comprises moisture present at not more than 10% of the final weight of the dosage form; d) the hardness of the dosage forth is from 0.5 kiloponds to 3 kiloponds; e) the dosage form comprises from 20 to 50 three-dimensionally printed incremental layers in stacked arrangement; or f) a combination thereof.

7. The dosage form of claim 6, wherein the average thickness of three-dimensionally printed incremental layer is from about 100 microns to about 400 microns.

8. The dosage form of claim 1, wherein the dosage form is shaped as a wafer, cylinder, ring, donut, tube, cube, spheroid, ellipsoid or rectangular box.

9. The dosage form of claim 1, wherein:
the wax: coated particles are present in an amount of 15% to 20% of the final weight of the non-compressed bound matrix;
the at least one wax is present in an amount of 20% to 30% of the final weight of the non-compressed bound matrix;
the at least one surfactant is present in an amount of 2.5% to 3.5% of the final weight of the non-compressed bound matrix;
the at least one water soluble, aqueous fluid soluble, partially water soluble or partially aqueous fluid soluble binder is present as at least one first binder and at least one second binder, wherein the at least one first binder is present in an amount of 4.5% to 10% of the final weight of the non-compressed bound matrix, and the at least one second binder is present in an amount of 25% to 50% of the final weight of the non-compressed bound matrix; and the non-compressed bound matrix further comprises:
at least one glidant present in an amount of 0.5% to 1.5% of the final weight of the non-compressed bound matrix;
at least one disintegrant present in an amount of 4.5% to 10% of the final weight of the non-compressed bound matrix; and
at least one sweetener present in an amount of 1% to 2% of the final weight of the non-compressed bound matrix.

10. A taste-masked rapidly dispersible dosage form comprising:
a solid porous non-compressed three-dimensionally printed bound matrix comprising:
spray-congealed taste-masked wax-coated particles comprising drug particles and at least one wax, wherein the spray-congealed taste-masked wax-coated particles have a weight ratio from 20:80 to 50:50, wherein the wax: coated particles are prepared by spray congealing a mixture of the drug particles and a molten form of the wax, and wherein the wax is not an ionic polymer or copolymer, an acrylate polymer or copolymer, a methacrylate polymer or copolymer, or an enteric polymer or copolymer;
at least one water soluble, aqueous fluid soluble, partially water soluble or partially aqueous fluid soluble binder selected from the group consisting of water soluble synthetic polymer, polyvinylpyrrolidone, hydroxypropylmethylcellulose, copovidone, pregelatinized cornstarch, hydroxypropylcellulose, lactose, fructose, sucrose, dextrose, sorbitol, mannitol, xylitol and a combination thereof;
and at least one surfactant independently selected upon each occurrence from the group consisting of polysorbate, poloxamer, sodium lauryl sulfate, and a combination thereof; and wherein,
the dosage form disperses in less than 90 sec when placed in aqueous fluid;
the total amount of wax-coated particles is from 20% to 50% of the final weight of the dosage form;
the wax-coated particles have an average or mean particle size of about 60 microns to about 250 microns; and
the drug particles have an average or mean particle size of about 30 microns to 50 microns;
whereby the drug remains taste-masked.

11. The dosage form of claim 10, wherein: a) the dosage form further comprises at least one sweetener present in an amount up to about 2% of the final weight of the dosage form; b) the at least one water soluble, aqueous fluid soluble, partially water soluble or partially aqueous fluid soluble binder is present in an amount up to about 20% of the final weight of the dosage form; c) the dosage form further comprises at least one disintegrant present in an amount up to about 30% of the final weight of the dosage form; d) the dosage form further comprises at least one glidant present in an amount up to about 2% of the final weight of the dosage form; e) the wax-coated particles further comprise more of the at least one surfactant.

12. The dosage form of claim 10, wherein: a) the hardness of the non-compressed bound matrix is up to about 1.0 kiloponds; b) the non-compressed bound matrix comprises from 10 to 40 three-dimensionally printed incremental layers in stacked arrangement; c) the hardness of the non-compressed bound matrix is from 0.5 kiloponds to 3 kiloponds; d) the non-compressed bound matrix comprises moisture present at not more than 10% of the final weight of the non-compressed bound matrix; or e) a combination thereof.

13. The dosage form of claim 11, wherein the wax-coated particles comprise at least one surfactant present at from 0.3% to 15% of the weight of wax-coated particles included in the dosage form.

14. A taste-masked rapidly dispersible dosage form comprising a three-dimensionally printed solid porous non-compressed bound matrix that disperses in less than 90 sec when placed in aqueous fluid, wherein the non-compressed bound matrix is prepared by a three-dimensional printing process comprising depositing aqueous printing fluid onto one or more layers of bulk powder, said bulk powder comprising:

taste-masked wax-coated particles comprising drug particles and at least one wax, wherein the taste-masked wax-coated particles have a drug-to-wax weight ratio from 20:80 to 50:50, and wherein the wax is not an ionic polymer or copolymer, an acrylate polymer or copolymer, a methacrylate polymer or copolymer, or an enteric polymer or copolymer;

at least one water soluble, aqueous fluid soluble, partially water soluble or partially aqueous fluid soluble binder selected from the group consisting of water soluble synthetic polymer, polyvinylpyrrolidone, hydroxypropylmethylcellulose, copovidone, pregelatinized cornstarch, hydroxypropylcellulose, lactose, fructose, sucrose, dextrose, sorbitol, mannitol, xylitol and a combination thereof; and wherein the printing fluid and/or the tasted-masked wax: coated particles of drug further comprise at least one surfactant independently selected upon each occurrence from the group consisting of polysorbate, poloxamer, sodium lauryl sulfate, and a combination thereof.

15. A rapidly dispersible dosage form comprising a three-dimensionally printed solid porous non-compressed bound three-dimensionally printed matrix comprising:

taste-masked wax-coated particles comprising a mixture comprising drug particles and at least one wax and having a drug-to-wax weight ratio ranging from 20:80 to 50:50, wherein the wax-coated particles have an average or mean particle size of from about 60 microns to about 250 microns;

at least one water soluble, aqueous fluid soluble, partially water soluble or partially aqueous fluid soluble binder selected from the group consisting of water soluble synthetic polymer, polyvinylpyrrolidone, hydroxypropylmethylcellulose, copovidone, pregelatinized cornstarch, hydroxypropylcellulose, lactose, fructose, sucrose, dextrose, sorbitol, mannitol, xylitol and a combination thereof;

at least one disintegrant; and at least one surfactant independently selected at each occurrence from the group consisting of polysorbate, poloxamer, sodium lauryl sulfate, and a combination thereof; wherein, the dosage form disperses in less than 90 sec when placed in aqueous fluid; and the dosage form comprises plural stacked three-dimensionally printed incremental layers, each layer having a thickness from 0.008 inches to 0.012 inches.

16. The rapidly dispersible dosage form of claim 15, wherein:

the at least one disintegrant is present in an amount up to 30% of the final weight of the dosage form;

the at least one surfactant is present in an amount up to 2% wt based upon the final weight of the dosage form;

the total amount of wax-coated particles is from 20% to 50% of the final weight of the dosage form; and the at least one water soluble, aqueous fluid soluble, partially water soluble or partially aqueous fluid soluble binder is present in an amount up to about 20% of the final weight of the dosage form.

* * * * *

UNITED STATES PATENT AND TRADEMARK OFFICE
CERTIFICATE OF CORRECTION

PATENT NO. : 10,420,785 B2  
APPLICATION NO. : 15/244563  
DATED : September 24, 2019  
INVENTOR(S) : Jules Jacob et al.

Page 1 of 1

It is certified that error appears in the above-identified patent and that said Letters Patent is hereby corrected as shown below:

In the Specification

Column 4, Line 11, delete "VIVID" and insert --VMD--.

Column 23, Line 49, delete "approximately 135,000." and insert --approximately 135,000. PVP K29/32 is polyvinylpyrrolidone exhibiting a k-value of 29-32.--.

Column 27, Line 62, delete "Mc" and insert --IIIc--.

In the Claims

Column 29, Claim 3, Line 24, delete "of drug".

Column 29, Claim 4, Line 26, delete "wax: coated" and insert --waxcoated--.

Column 29, Claim 6, Line 39, delete "forth" and insert --form--.

Column 29, Claim 9, Line 50, delete "wax: coated" and insert --waxcoated--.

Column 30, Claim 10, Line 20, delete "wax: coated" and insert --waxcoated--.

Column 31, Claim 14, Line 31, delete "wax: coated" and insert --waxcoated--.

Signed and Sealed this  
Eighteenth Day of February, 2020

Andrei Iancu  
*Director of the United States Patent and Trademark Office*